United States Patent
Okazaki et al.

(10) Patent No.: US 8,401,702 B2
(45) Date of Patent: Mar. 19, 2013

(54) ROBOT, AND CONTROL APPARATUS, CONTROL METHOD, AND CONTROL PROGRAM FOR ROBOT

(75) Inventors: Yasunao Okazaki, Shiga (JP); Atsushi Ono, Kyoto (JP); Katsuhiko Asai, Nara (JP)

(73) Assignee: Panasonic Corporation, Osaka (JP)

( * ) Notice: Subject to any disclaimer, the term of this patent is extended or adjusted under 35 U.S.C. 154(b) by 369 days.

(21) Appl. No.: 12/935,603

(22) PCT Filed: Jun. 2, 2009

(86) PCT No.: PCT/JP2009/002456
§ 371 (c)(1),
(2), (4) Date: Sep. 30, 2010

(87) PCT Pub. No.: WO2009/147832
PCT Pub. Date: Dec. 10, 2009

(65) Prior Publication Data
US 2011/0029133 A1  Feb. 3, 2011

(30) Foreign Application Priority Data

Jun. 6, 2008 (JP) .................................. 2008-148946

(51) Int. Cl.
*G05B 19/18* (2006.01)
*G05B 19/00* (2006.01)
(52) U.S. Cl. ........ 700/260; 700/257; 700/258; 700/264; 901/9; 901/11
(58) Field of Classification Search .................. None
See application file for complete search history.

(56) References Cited

U.S. PATENT DOCUMENTS

| 5,915,673 | A | * | 6/1999 | Kazerooni | .................... 254/270 |
| 5,996,150 | A | * | 12/1999 | Blevins et al. | .................... 5/613 |
| 6,204,619 | B1 | * | 3/2001 | Gu et al. | .................. 318/568.11 |
| 6,216,056 | B1 | * | 4/2001 | Ito et al. | ........................ 700/157 |

(Continued)

FOREIGN PATENT DOCUMENTS

| JP | 61-252084 | 11/1986 |
| JP | 63-200986 | 8/1988 |

(Continued)

OTHER PUBLICATIONS 00525894.pdf (Kazushige Kakutani, Tsunehito Iwaki, Daizo Takaoka, Makoto Yamada, Kazuyoshi Tsukamoto, Development of a Transfer Supporting Equipment, 1995, IEEE, pp. 268-273).*

(Continued)

*Primary Examiner* — Khoi Tran
*Assistant Examiner* — Bao Long T Nguyen
(74) *Attorney, Agent, or Firm* — Wenderoth, Lind & Ponack, L.L.P.

(57) ABSTRACT

A robot arm provided with a body unit shifting mechanism that connects a base unit and a body unit so as to be relatively shifted, and joint lock mechanisms that are capable of mechanically securing respective joints is disposed on the body unit, and a robot operation control unit controls to switch between a robot arm operation mode in which the robot arm is operated with one of the joints of the robot arm brought into a free state, and a body unit shift mode in which the body unit is shifted with the joint being brought into a locked state.

13 Claims, 23 Drawing Sheets

U.S. PATENT DOCUMENTS

| | | | |
|---|---|---|---|
| 6,385,508 B1 * | 5/2002 | McGee et al. | 700/254 |
| 6,386,513 B1 * | 5/2002 | Kazerooni | 254/270 |
| 6,394,731 B1 * | 5/2002 | Konosu et al. | 414/5 |
| 6,430,473 B1 * | 8/2002 | Lee et al. | 700/245 |
| 6,837,883 B2 * | 1/2005 | Moll et al. | 606/1 |
| 7,395,606 B2 * | 7/2008 | Crampton | 33/503 |
| 8,226,072 B2 * | 7/2012 | Murayama | 269/55 |
| 2002/0082612 A1 * | 6/2002 | Moll et al. | 606/130 |
| 2003/0135303 A1 * | 7/2003 | Arai et al. | 700/245 |

FOREIGN PATENT DOCUMENTS

| | | |
|---|---|---|
| JP | 6-297366 | 10/1994 |
| JP | 6-320451 | 11/1994 |
| JP | 9-038150 | 2/1997 |
| JP | 11-309184 | 11/1999 |
| JP | 2001-269370 | 10/2001 |
| JP | 2003-011079 | 1/2003 |
| JP | 2003-136440 | 5/2003 |
| JP | 2004-358575 | 12/2004 |
| JP | 2007-252469 | 10/2007 |
| JP | 2008-086542 | 4/2008 |
| JP | 2008-100053 | 5/2008 |

OTHER PUBLICATIONS

International Search Report issued Aug. 25, 2009 in International (PCT) Application No. PCT/JP2009/002456.

International Preliminary Report on Patentability (Chapter II) (in English) issued Jan. 20, 2011 in International (PCT) Application No. PCT/JP2009/002456.

T. Odashima, "Development and Evaluation of a Human-interactive Robot Platform 'RI-MAN'", Journal of the Robotics Society of Japan, vol. 25, No. 4, May 15, 2007, pp. 70-81 (with English Abstract).

Panasonic Corp., Dai 34 Kai Kokusai Fukushi Kikiten/Transfer Assist Robot to Rehabilitation Shien, Panasonic Group no Broadband Hoso Channel Panasonic, Panasonic Corp., Oct. 11, 2007.

* cited by examiner

Fig. 15

| OPERATION SEQUENCE | LEFT ARM | | RIGHT ARM | | WAIST MECHANISM |
| --- | --- | --- | --- | --- | --- |
| | CONTROL MODE | JOINT LOCK | CONTROL MODE | JOINT LOCK | CONTROL MODE |
| SEQUENCE 1: HOME POSITION | POSITION CONTROL | FREE | POSITION CONTROL | FREE | ANGLE CONTROL |
| SEQUENCE 2: LEFT ARM OPERATION | IMPEDANCE CONTROL | FREE | POSITION CONTROL | FREE | ANGLE CONTROL |
| SEQUENCE 3: RIGHT ARM OPERATION | POSITION CONTROL | FREE | IMPEDANCE CONTROL | FREE | ANGLE CONTROL |
| SEQUENCE 4: JOINT LOCK | POSITION CONTROL | SECURED | POSITION CONTROL | SECURED | ANGLE CONTROL |
| SEQUENCE 5: LIFTING | POSITION CONTROL | SECURED | POSITION CONTROL | SECURED | IMPEDANCE CONTROL |
| SEQUENCE 6: RELEASE JOINT LOCK | POSITION CONTROL | FREE | POSITION CONTROL | FREE | ANGLE CONTROL |
| SEQUENCE 7: LEFT ARM SEPARATED | IMPEDANCE CONTROL | FREE | POSITION CONTROL | FREE | ANGLE CONTROL |
| SEQUENCE 8: RIGHT ARM SEPARATED | POSITION CONTROL | FREE | IMPEDANCE CONTROL | FREE | ANGLE CONTROL |

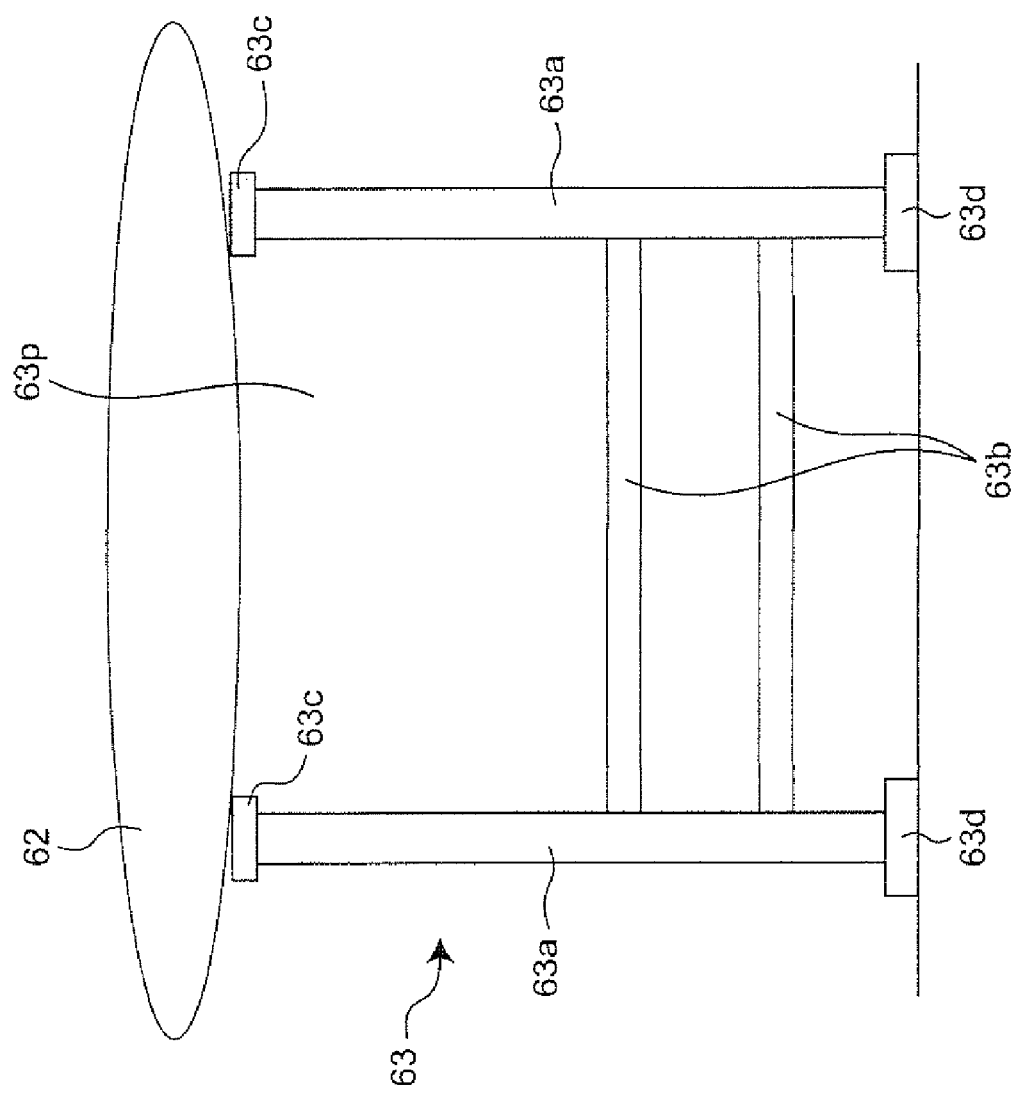

ROBOT, AND CONTROL APPARATUS, CONTROL METHOD, AND CONTROL PROGRAM FOR ROBOT

TECHNICAL FIELD

The present invention relates to a robot that carries out a lift-up operation of a heavy object, such as a lift-up job in nursing care or a transporting operation of an article, or a transporting operation or the like, as well as a control apparatus, a control method, and a control program for such a robot.

BACKGROUND ART

In the recent aged society, there have been demands for development of an apparatus capable of giving an assist, such as nursing care, or a power assist apparatus or the like used for assisting an elder person to carry out a house-keeping job.

In view of these demands, there has been disclosed, as a conventional technique, a movable lift for nursing care, which is movable even in a narrow passage without requiring much labor of a care giver, and usable and available even in a small-size facility in a simple structure at low costs (see Patent Document 1). Moreover, there has been disclosed a transfer-lifting machine, composed of lift-up arms that support arms of a care giver, an arm driving mechanism composed of a geared motor and a worm jack for raising and lowering the lift-up arms, and a tape switch that detects a load of a cared person (see Patent Document 2).

PRIOR ART DOCUMENTS

Patent Documents
Patent Document 1: Japanese Unexamined Patent Publication No. H09-38150
Patent Document 2: Japanese Unexamined Patent Publication No. 2001-269370

DISCLOSURE OF INVENTION

Subject to be Solved by the Invention

However, the conventional device disclosed in Patent Document 1 has an issue that, since manual operations are required, operability is poor to cause degradation of work efficiency. Moreover, even when an actuator such as a motor is added to provide automatic operations for improvement of the work efficiency, the device becomes bulky and heavier, thereby failing to be applied to a general household environment.

Moreover, in the conventional device disclosed in Patent Document 2, since the position of a care giver, that is an operator, is limited to a chair of the device, and since, upon a lift-up operation, hands of the care giver are located beneath the cared person and unable to move freely, it is not possible to carry out another job simultaneously for example, thereby failing to provide usability.

It is an object of the present invention to provide a robot that can solve the issues of the conventional devices, is highly powerful as well as light weighted, and applicable to a lift-up job in nursing care or a transporting operation of a heavy object, and also has superior operability, usability and high work efficiency, as well as to provide a control apparatus, a control method, and a control program for such a robot.

Means for Solving the Subject

In order to achieve the above-mentioned object, the present invention proposes the following structures.

According to a first aspect of the present invention, there is provided a robot comprising:
a base unit;
a body unit;
a body unit shifting mechanism that connects the base unit to the body unit by a waist joint, and relatively shifts the body unit relative to the base unit;
a robot arm that is disposed on the body unit, and has a plurality of links and joint lock mechanisms capable of respectively mechanically securing a joint coupling the plurality of links to one another and a joint coupling one of the plurality of links and the body unit;
an actuator for the robot arm, that drives the respective joints of the robot arm so as to drive to pivot the plurality of links;
an actuator for the waist joint, that drives the body unit through the body unit shifting mechanism so as to relatively shift relative to the base unit;
actuators for the joint lock mechanisms, that drives the joint lock mechanisms; and
a robot operation control unit that drive-controls the actuators for the joint lock mechanisms, the actuator for the robot arm, and the actuator for the waist joint respectively, and switches between a robot arm operation mode in which the robot arm is operated with one of the joints of the robot arm being brought into a free state, and a body unit shift mode in which the body unit is shifted by using the body unit shifting mechanism with one of the joints of the robot arm being brought into a locked state.

According to a 10th aspect of the present invention, there is provided a robot control apparatus for controlling an operation of a robot comprising: a base unit; a body unit; a body unit shifting mechanism that connects the base unit to the body unit by a waist joint, and relatively shifts the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the respective joints of the robot arm so as to drive to pivot the plurality of links; an actuator for the waist joint, that drives the body unit through the body unit shifting mechanism so as to relatively shift relative to the base unit; and actuators for the joint lock mechanisms, that drives the joint lock mechanisms,
the actuators for the joint lock mechanisms, the actuator for the robot arm, and the actuator for the waist joint being respectively drive-controlled to switch between a robot arm operation mode in which the robot arm is operated with one of the joints of the robot arm being brought into a free state, and a body unit shift mode in which the body unit is shifted by using the body unit shifting mechanism with one of the joints of the robot arm being brought into a locked state.

According to an 11th aspect of the present invention, there is provided a robot control method for controlling an operation of a robot comprising: a base unit; a body unit; a body unit shifting mechanism that connects the base unit to the body unit by a waist joint, and relatively shifts the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the respective joints of the robot arm so as to drive to pivot the plurality of links; an actuator for the waist joint, that drives the body unit through the body unit shifting mechanism so as to relatively shift relative to the base unit; and actuators for the joint lock mechanisms, that drives the joint lock mechanisms, the method comprising: respectively drive-controlling the actuators for the joint lock mechanisms, the actuator for the robot arm, and the actuator for the waist joint and thus switching between a robot arm operation mode in which the robot arm is operated with one of the joints of the robot arm being brought into a free state, and a body unit shift mode in which the body unit is shifted by using the body unit shifting mechanism with one of the joints of the robot arm being brought into a locked state.

According to a 12th aspect of the present invention, there is provided a robot control program for controlling an operation of a robot comprising: a base unit; a body unit; a body unit shifting mechanism that connects the base unit to the body unit by a waist joint, and relatively shifts the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the respective joints of the robot arm so as to drive to pivot the plurality of links; an actuator for the waist joint, that drives the body unit through the body unit shifting mechanism so as to relatively shift relative to the base unit; and actuators for the joint lock mechanisms, that drives the joint lock mechanisms, the control program allowing a computer to function as a robot operation control unit such that the actuators for the joint lock mechanisms, the actuator for the robot arm, and the actuator for the waist joint are respectively drive-controlled so as to switch between a robot arm operation mode in which the robot arm is operated with one of the joints of the robot arm being brought into a free state, and a body unit shift mode in which the body unit is shifted by using the body unit shifting mechanism with one of the joints of the robot arm being brought into a locked state.

Effects of the Invention

In accordance with the robot of the present invention, since the joint lock mechanism is included, a weight load of a transporting object can be held mechanically, the light weighted arm can be achieved. Moreover, since the joints are made free by the joint lock mechanism, a high degree of freedom achieved by the arm structure is effectively utilized so that the degree of freedom in positioning relative to the transporting object is made higher, thereby providing the easily usable robot.

Moreover, in accordance with the robot of the present invention, since the waist mechanism is included in addition to the robot arm provided with the joint lock mechanism, the powerful actuator for lifting up a heavy object is only required to the waist mechanism so that the high-power robot can be achieved in a simple and light weighted structure.

Furthermore, in accordance with the robot of the present invention, since there is included the robot operation control means for controlling the operations, while switching modes between the impedance control mode and the position control mode, as well as switching the locking and lock-releasing operations of the joint lock mechanism, operations such as positioning of the arm and lifting up of a transporting object can be carried out continuously, and since the impedance control is carried out by the external detection device included (for example, a force sensor), it becomes possible to realize an operation method that is easily understood by an operator in an intuitive manner, that is, an operation method that allows the operator to directly operate the arm with a hand, thereby providing the robot that is further easily used.

In accordance with the control apparatus, control method, and control program for a robot of the present invention, in a case where, the joints are made free (released from the locked state) by controlling the locking and lock-releasing operations of the joint lock mechanism that can mechanically hold a weight load of a transporting object, it is possible to effectively utilize the high degree of freedom achieved by the arm structure having the plurality of links with the joints interpolated therebetween while achieving the light weighted arm, and consequently to increase the degree of freedom in positioning relative to the transporting object. Thus, it becomes possible to easily control and use the robot.

In accordance with the control apparatus, control method, and control program for a robot of the present invention, by carrying out operation controls on the waist mechanism in addition to operation controls on the joint lock mechanism, the powerful actuator used for lifting up a heavy object is only required for operation controlling the waist mechanism so that the high-power robot can be achieved in a simple and light weighted structure.

In accordance with the control apparatus, control method, and control program for a robot of the present invention, the robot operations can be controlled while switching between the impedance control mode and the position control mode as well as switching the operations of the joint lock mechanism so that the operations, such as positioning the arm and lifting up a transporting object, can be carried out continuously, as well as by carrying out the impedance control based upon information of an external force from the external force detection device (for example, a force sensor), it becomes possible to realize the operation method that is easily understood in an intuitive manner, that is, the operation method by which the operator is allowed to directly operate the arm with a hand, thereby providing a robot that is further easily used.

BRIEF DESCRIPTION OF DRAWINGS

These and other aspects and features of the present invention will become clear from the following description taken in conjunction with the preferred embodiments thereof with reference to the accompanying drawings, in which:

FIG. 15 is a view of an operation sequence chart that shows switching steps of operation modes of the control apparatus of the robot according to the embodiment of the present invention;

FIG. 18 is a view for explaining supporting legs of the robot according to the embodiment of the present invention;

DESCRIPTION OF EMBODIMENTS

Figure 1:
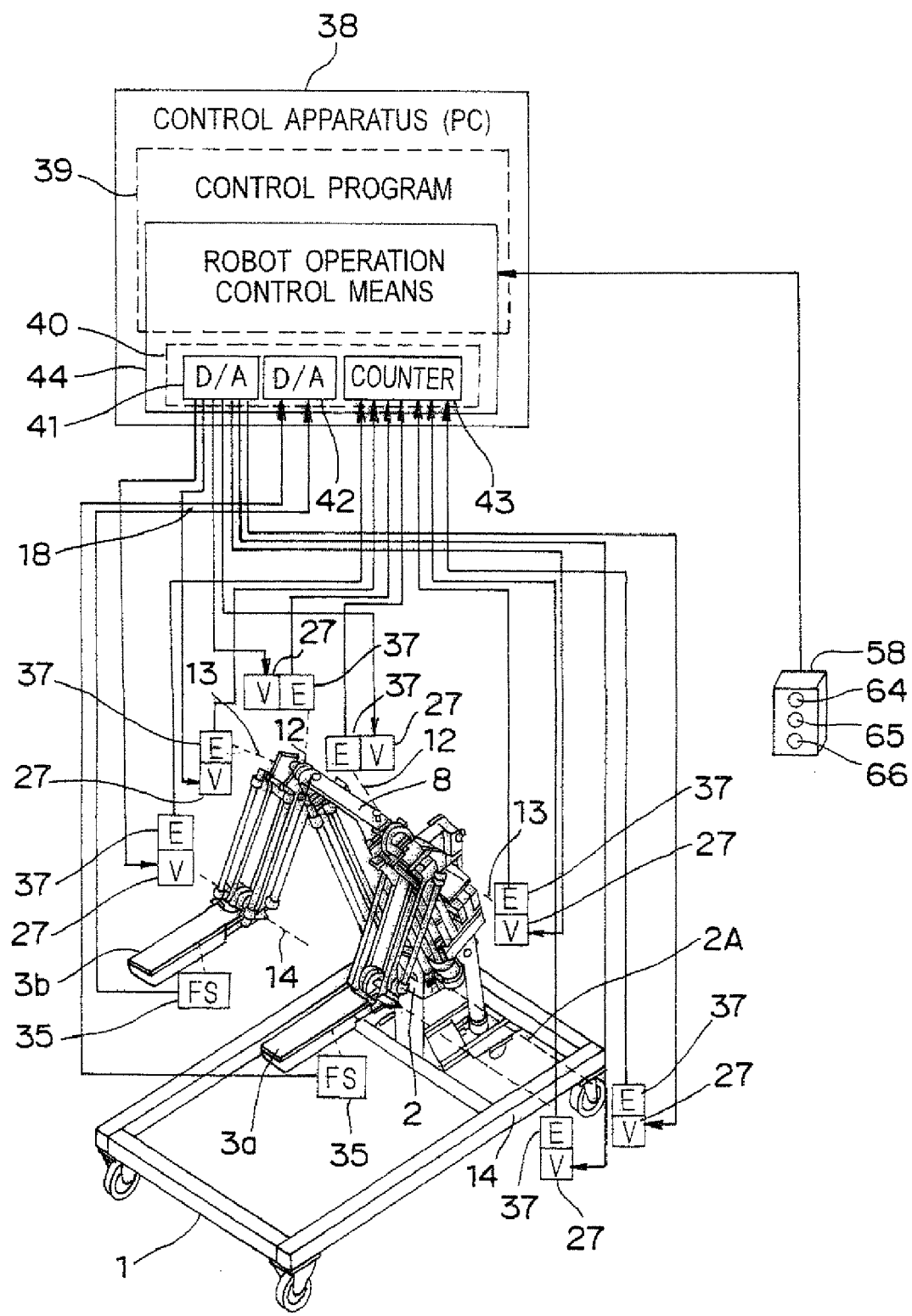
FIG. 1 is an explanatory view that shows a schematic structure of a robot according to one embodiment of the present invention.

Referring to the drawings, the following description will discuss in detail embodiments of the present invention.

Prior to detailed explanations of the embodiments of the present invention with reference to the drawings, various modes of the present invention will be explained.

According to a first aspect of the present invention, there is provided a robot comprising:

a base unit;

a body unit;

a body unit shifting mechanism that connects the base unit to the body unit by a waist joint, and relatively shifts the body unit relative to the base unit;

a robot arm that is disposed on the body unit, and has a plurality of links and joint lock mechanisms capable of respectively mechanically securing a joint coupling the plurality of links to one another and a joint coupling one of the plurality of links and the body unit;

an actuator for the robot arm, that drives the respective joints of the robot arm so as to drive to pivot the plurality of links;

an actuator for the waist joint, that drives the body unit through the body unit shifting mechanism so as to relatively shift relative to the base unit;

actuators for the joint lock mechanisms, that drives the joint lock mechanisms; and a robot operation control unit that drive-controls the actuators for the joint lock mechanisms, the actuator for the robot arm, and the actuator for the waist joint respectively, and switches between a robot arm operation mode in which the robot arm is operated with one of the joints of the robot arm being brought into a free state, and a body unit shift mode in which the body unit is shifted by using the body unit shifting mechanism with one of the joints of the robot arm being brought into a locked state.

According to a second aspect of the present invention, there is provided the robot according to the first aspect, wherein the actuator for the robot arm is a pneumatic artificial muscle, and the actuator for the waist joint is a pneumatic artificial muscle, the robot arm is provided with an external force detection device that detects an external force applied to the robot arm, and based upon the external force applied to the robot arm detected by the external force detection device, the robot operation control unit drive-controls the pneumatic artificial muscle as the actuator for the robot arm and the pneumatic artificial muscle as the actuator for the waist joint, so that the robot arm is operation-controlled in the robot arm operation mode and the body unit is shift-controlled in the body unit shift mode.

According to a third aspect of the present invention, there is provided the robot according to the second aspect, wherein the robot operation control unit operation-controls the arm and shift-controls the body unit based upon the external force by an impedance control.

According to a fourth aspect of the present invention, there is provided the robot according to the second aspect, wherein the robot arm has an external covering member that is disposed in a farthest tip end link out of the plurality of links so as to cover substantially a half of an external surface of a cross section in a width direction of the farthest tip end link and substantially an overall length in a longitudinal direction thereof, and the external force detection device detects an external force applied to the external covering member.

According to a fifth aspect of the present invention, there is provided the robot according to any one of the first to fourth aspects, wherein the body unit shifting mechanism is a waist mechanism that rocks the body unit substantially forward and rearward around the waist joint relative to the base unit.

According to a sixth aspect of the present invention, there is provided the robot according to the fifth aspect, wherein the waist mechanism has one end secured to the base unit and another end secured to the body unit so as to be driven by a translation driving actuator that drives the waist joint and rock the body unit substantially forward and rearward around the waist joint relative to the base unit.

According to a seventh aspect of the present invention, there is provided the robot according to the first aspect, wherein the joint lock mechanism is a one-way clutch mechanism.

According to an eighth aspect of the present invention, there is provided the robot according to the seventh aspect, wherein, when the joint lock mechanism is in a locked state, the robot operation control unit carries out on one of the joints the robot arm operation mode in response to an external force exerted in a movable direction of the one-way clutch mechanism, and does not carry out the robot arm operation mode in response to an external force exerted in a non-movable direction of the one-way clutch mechanism.

According to a ninth aspect of the present invention, there is provided the robot according to the seventh aspect, wherein, when the joint lock mechanism is in a locked state, the robot operation control unit carries out a position control operation on the robot arm by using a servo rigidity lower than a servo rigidity in a non-locked state.

According to a 10th aspect of the present invention, there is provided a robot control apparatus for controlling an operation of a robot comprising: a base unit; a body unit; a body unit shifting mechanism that connects the base unit to the body unit by a waist joint, and relatively shifts the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the respective joints of the robot arm so as to drive to pivot the plurality of links; an actuator for the waist joint, that drives the body unit through the body unit shifting mechanism so as to relatively shift relative to the base unit; and actuators for the joint lock mechanisms, that drives the joint lock mechanisms, the actuators for the joint lock mechanisms, the actuator for the robot arm, and the actuator for the waist joint being respectively drive-controlled to switch between a robot arm operation mode in which the robot arm is operated with one of the joints of the robot arm being brought into a free state, and a body unit shift mode in which the body unit is shifted by using the body unit shifting mechanism with one of the joints of the robot arm being brought into a locked state.

According to an 11th aspect of the present invention, there is provided a robot control method for controlling an operation of a robot comprising: a base unit; a body unit; a body unit shifting mechanism that connects the base unit to the body unit by a waist joint, and relatively shifts the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the respective joints of the robot arm so as to drive to pivot the plurality of links; an actuator for the waist joint, that drives the body unit through the body unit shifting mechanism so as to relatively shift relative to the base unit; and actuators for the joint lock mechanisms, that drives the joint lock mechanisms, the method comprising: respectively drive-controlling the actuators for the joint lock mechanisms, the actuator for the robot arm, and the actuator for the waist joint and thus switching between a robot arm operation mode in which the robot arm is operated with one of the joints of the robot arm being brought into a free state, and a body unit shift mode in which the body unit is shifted by using the body unit shifting mechanism with one of the joints of the robot arm being brought into a locked state.

According to a 12th aspect of the present invention, there is provided a robot control program for controlling an operation of a robot comprising: a base unit; a body unit; a body unit shifting mechanism that connects the base unit to the body unit by a waist joint, and relatively shifts the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the respective joints of the robot arm so as to drive to pivot the plurality of links; an actuator for the waist joint, that drives the body unit through the body unit shifting mechanism so as to relatively shift relative to the base unit; and actuators for the joint lock mechanisms, that drives the joint lock mechanisms, the control program allowing a computer to function as a robot operation control unit such that the actuators for the joint lock mechanisms, the actuator for the robot arm, and the actuator for the waist joint are respectively drive-controlled so as to switch between a robot arm operation mode in which the robot arm is operated with one of the joints of the robot arm being brought into a free state, and a body unit shift mode in which the body unit is shifted by using the body unit shifting mechanism with one of the joints of the robot arm being brought into a locked state.

Referring to the drawings, the following description will discuss in detail the embodiments of the present invention.

(Embodiment 1)

Figure 2:
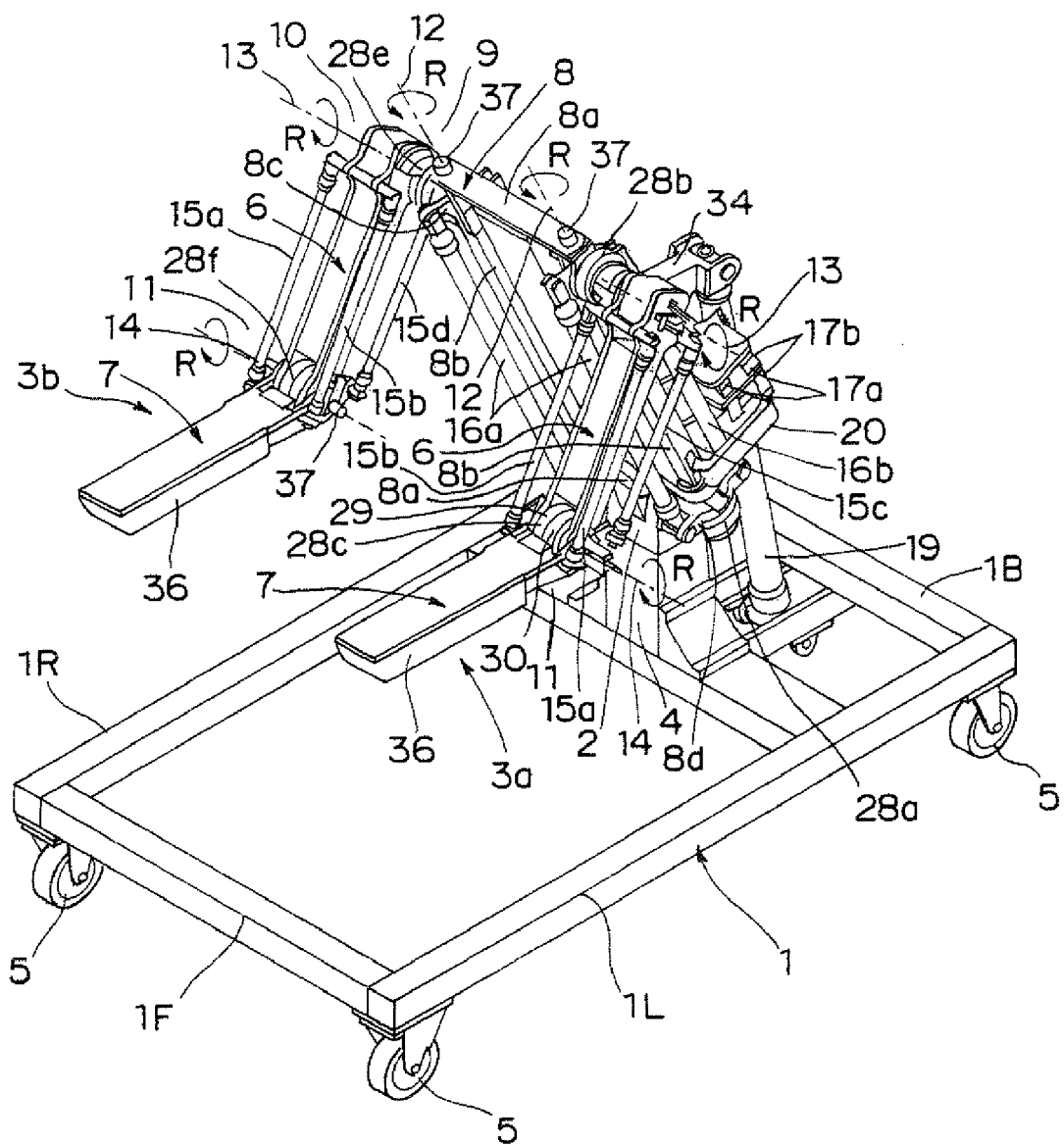
FIG. 2 is a perspective view that shows a mechanical structure of the robot according to the embodiment of the present invention.
Figure 3:
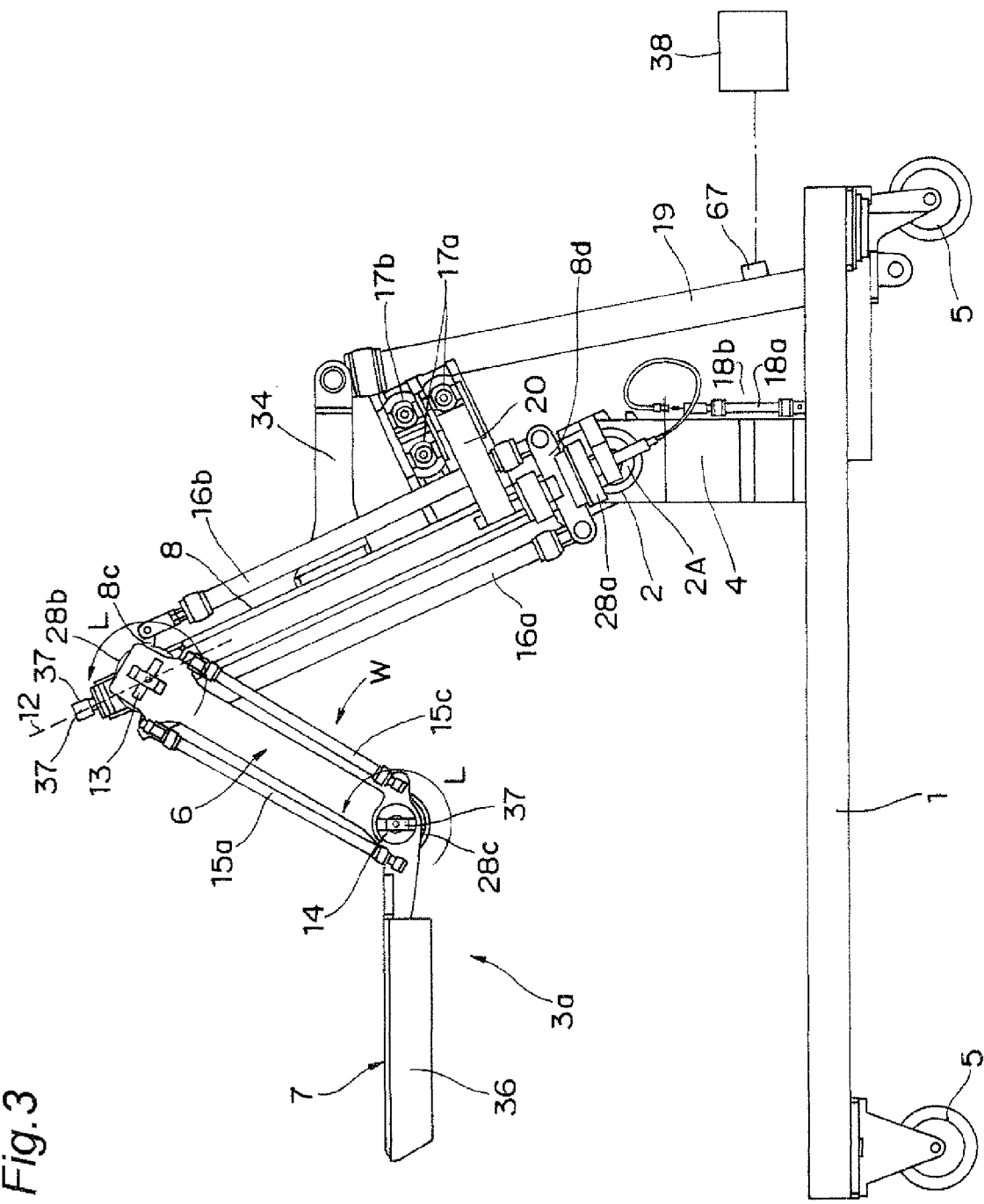
FIG. 3 is a side view that shows the mechanical structure of the robot according to the embodiment of the present invention.

FIG. 1 is a view that shows a schematic structure of a robot according to a first embodiment of the present invention. FIG. 2 is a perspective view that shows a mechanical structure of the robot. FIG. 3 is a side view of the robot.

The robot is composed of five blocks, namely, a base unit 1 having a rectangular frame shape, a waist mechanism 2 that functions as one example of a body unit moving mechanism secured to the base unit 1, a body unit 8 supported by the waist mechanism 2, a left arm 3a supported on the left side of the body unit 8, and a right arm 3b supported on the right side of the body unit 8.

On the upper surface of the base unit 1 forming a base of the robot, a rectangular parallelepiped strut 4 is placed, and the waist mechanism 2 is placed on the upper portion of the strut 4. Moreover, wheels 5 are placed at four corners of the base unit 1 respectively so that the entire robot is movable.

The waist mechanism 2 is composed of rotation joints (waist joints) around a waist rotation axis 2A, and connects the base unit 1 with the body unit 8 so that the body unit 8 is allowed to rock forward and rearward relative to the base unit 1, by the waist mechanism 2. Since the base unit 1 has the rectangular shape, one of opposed shorter sides of the base unit 1 is defined as a front end portion (end portion 1F on the left front side of FIG. 2), and the other side is defined as a rear end portion (end portion 1B on the right rear side of FIG. 2). Thus, relative to the front end portion 1F, the end portion on the right side (end portion on one of opposed longer sides of the base unit 1) is defined as a right end portion 1R, and the end portion on the left side (end portion on the other one of the opposed longer sides of the base unit 1) is defined as a left end portion 1R, respectively.

The body unit 8 is composed of a square frame member formed by a pair of square-pillar shaped longitudinal frame members 8a, a pair of square-pillar shaped lateral frame members 8b, and on upper end portions of the body unit 8, a left arm 3a and a right arm 3b are respectively installed on side surfaces independently so as to rotate thereon. The right arm 3b and the left arm 3a are symmetrical with each other, and both of the arms 3a and 3b have the same structure; therefore, upon explaining the structures or the like of the arms 3a and 3b in the following description, the arm 3 is explained as a typical example.

The arm 3 has a two-link structure including a first link 6 serving as an upper arm and a second link 7 serving as a fore-arm. The base end portion of the first link 6 is connected to the upper end portion of the body unit 8 through a first joint 9 and a second joint 10 serving as shoulder joints so as to be pivotable relative to the base unit 8 around the axis of the first joint 9 and the axis of the second joint 10. That is, the first link 6 is pivotable around the first joint axis 12 along the axis direction of each of the longitudinal frame members 8a of the body unit 8 by the first joint 9, and the first link 6 is also pivotable around a second joint axis 13 along the axis direction of each of the lateral frame members 8b on the upper side of the body unit 8 by the second joint 10. Moreover, the tip end portion of the first link 6 and the base end portion of the second link 7 are pivotable relative to each other by a third joint 11 serving as an elbow joint. The second link 7 is pivotable around a third joint axis 14 in parallel with the second joint axis 13 relative to the first link 6 by the third joint 11.

An encoder 37 serving as one example of a joint angle sensor is attached to each of the first joint 9, the second joint 10, and the third joint 11 of the arm 3 so as to detect a rotation angle (joint angle vector) $q=[q_1, q_2, q_3]^T$ of each of the joints 9, 10, and 11. In this case, $q_1$, $q_2$, and $q_3$ are joint angles of the first joint 9, the second joint 10, and the third joint 11, respectively. Information of the rotation angle detected by the encoder 37 is outputted to a control apparatus 38.

Symbols, 15a, 15b, 15c, 15d, 16a, 16b, 17a, 17b, 17c, 17d, 18a, 18b, 18c, 18d, 18e, and 18f represent pneumatic artificial muscles, and by changing the air pressure inside each of the pneumatic artificial muscles, the muscle is contracted and expanded to function as one example of a robot arm actuator that drives each of the joints 6, 10, 11, and 2A of the left arm 3a, the right arm 3b, and the waist mechanism 2. The pneumatic artificial muscles 15a, 15b, 15c, and 15d function as third joint driving members of the arm which drive rotation movements around the third joint axis 14 by the third joint 11. The pneumatic artificial muscles 16a and 16b function as second joint driving members of the arm which drive rotation movements around the second joint axis 13 by the second joint 10. The pneumatic artificial muscles 17a, 17b, 17c, and 17d function as first joint driving members of the arm which drive rotation movements around the first joint axis 12 by the first joint 9. The pneumatic artificial muscles 18a, 18b, 18c, 18d, 18e, and 18f function as lock operation driving members that drive lock operations of a joint lock mechanism 28, which will be described later.

Symbol 19 is a pneumatic artificial muscle that functions as one example of an actuator for a waist joint or a waist mechanism driving member, and the pneumatic artificial muscle 19 functions as a translation driving actuator that drives rotation movements around the joint axis 2A of the waist mechanism 2.

Next, the following description will discuss the driving mechanism by the pneumatic artificial muscles 15a, 15b, 15c, 15d, 16a, 16b, 17a, 17b, 17c, and 17d, by exemplifying rotation movements around the third joint axis 14 by the third joint 11. The pneumatic artificial muscles 15a and 15b are disposed on the front side of the first link 6 as well as on the respective sides thereof, and the pneumatic artificial muscles 15c and 15d are disposed on the rear side of the first link 6 as well as on the respective sides thereof. Each of the pneumatic artificial muscles 15a, 15b, 15c, and 15d has one end portion (end portion on the upper side) secured onto the base end portion of the first link 6 so as to freely rotate thereon near the second joint 10, and also has the other end portion (end portion on the lower side) secured to the base end portion of the second link 7 so as to freely rotate thereon near the third joint 11. Moreover, on the base end portion of the second link 7, the other end portions of the pneumatic artificial muscles 15a and 15b on the front side and the other end portions of the pneumatic artificial muscles 15c and 15d on the rear side are respectively secured onto symmetrical positions centered on the third joint axis 14 of the third joint 11. Thus, by respectively changing the inner air pressures of the pneumatic artificial muscles 15a and 15b on the front side and the pneumatic artificial muscles 15c and 15d on the rear side, the pneumatic artificial muscles 15a and 15b and the pneumatic artificial muscles 15c and 15d are contracted and expanded, so that the pneumatic artificial muscles 15a and 15b and the pneumatic artificial muscles 15c and 15d are allowed to balance with each other. Thus, a rotation movement around the third joint axis 14 of the third joint 11 is generated so that relative movements of the first link 6 and the second link 7 are driven. For example, when driving operations are exerted so that the pneumatic artificial muscles 15a and 15b on the front side are expanded, with the pneumatic artificial muscles 15c and 15d on the rear side being contracted, the second link 7 is allowed to pivot clockwise around the third joint axis 14 of the third joint 11 relative to the first link 6, as shown in FIG. 2. In contrast, when driving operations are exerted so that the pneumatic artificial muscles 15a and 15b on the front side are contracted, with the pneumatic artificial muscles 15c and 15d on the rear side being expanded, the second link 7 is allowed to pivot anticlockwise around the third joint axis 14 of the third joint 11 relative to the first link 6, as shown in FIG. 2.

In the same manner, rotation movements around the second joint axis 13 of the second joint 10 are driven by the balancing driving operations of the pneumatic artificial muscle 16a on the front side and the pneumatic artificial muscle 16b on the rear side. That is, two pneumatic artificial muscles 16a on the front side are disposed on the front side of the body unit 8 near the longitudinal frame member 8a, and two pneumatic artificial muscles 16b on the rear side are disposed on the rear side of the body unit 8 near the longitudinal frame member 8a. The pneumatic artificial muscles 16a and 16b have one end portions (end portions on the upper side) secured respectively to two end portions of an upper-side rod-shaped link member 8c secured to the base end portion of the upper link 6 near the second joint 10 so as to be rotatable thereon, and also have the other end portions (end portions on the lower side) secured respectively to two end portions of a lower-side rod-shaped link member 8*d* secured to the lower end portion of the body unit 8 near the rotation axis 2A of the waist mechanism 2. Moreover, the other end portion of the pneumatic artificial muscle 16*a* on the front side and the other end portion of the pneumatic artificial muscle 16*b* on the rear side are respectively disposed at symmetrical positions with each other. For this reason, by respectively changing the inner air pressures of the pneumatic artificial muscle 16*a* on the front side and the pneumatic artificial muscle 16*b* on the rear side, the pneumatic artificial muscle 16*a* and the pneumatic artificial muscle 16*b* are contracted and expanded so that the pneumatic artificial muscle 16*a* and the pneumatic artificial muscle 16*b* are allowed to balance with each other. Thus, a rotation movement around the second joint axis 13 of the second joint 10 is generated so that relative rotation movements of the body unit 8 and the arm are driven. For example, when driving operations are exerted so that the pneumatic artificial muscles 16*a* on the front side is expanded with the pneumatic artificial muscles 16*b* on the rear side being contracted, the arm 3 is allowed to pivot anticlockwise around the second joint axis 13 of the second joint 10 relative to the body unit 8, as shown in FIG. 2, and consequently to pivot rearward. In contrast, when driving operations are exerted so that the pneumatic artificial muscle 16*a* on the front side is contracted with the pneumatic artificial muscle 16*b* on the rear side being expanded, the arm 3 is allowed to pivot clockwise around the second joint axis 13 of the second joint 10 relative to the body unit 8, as shown in FIG. 2, and consequently to pivot forward.

Figure 22:
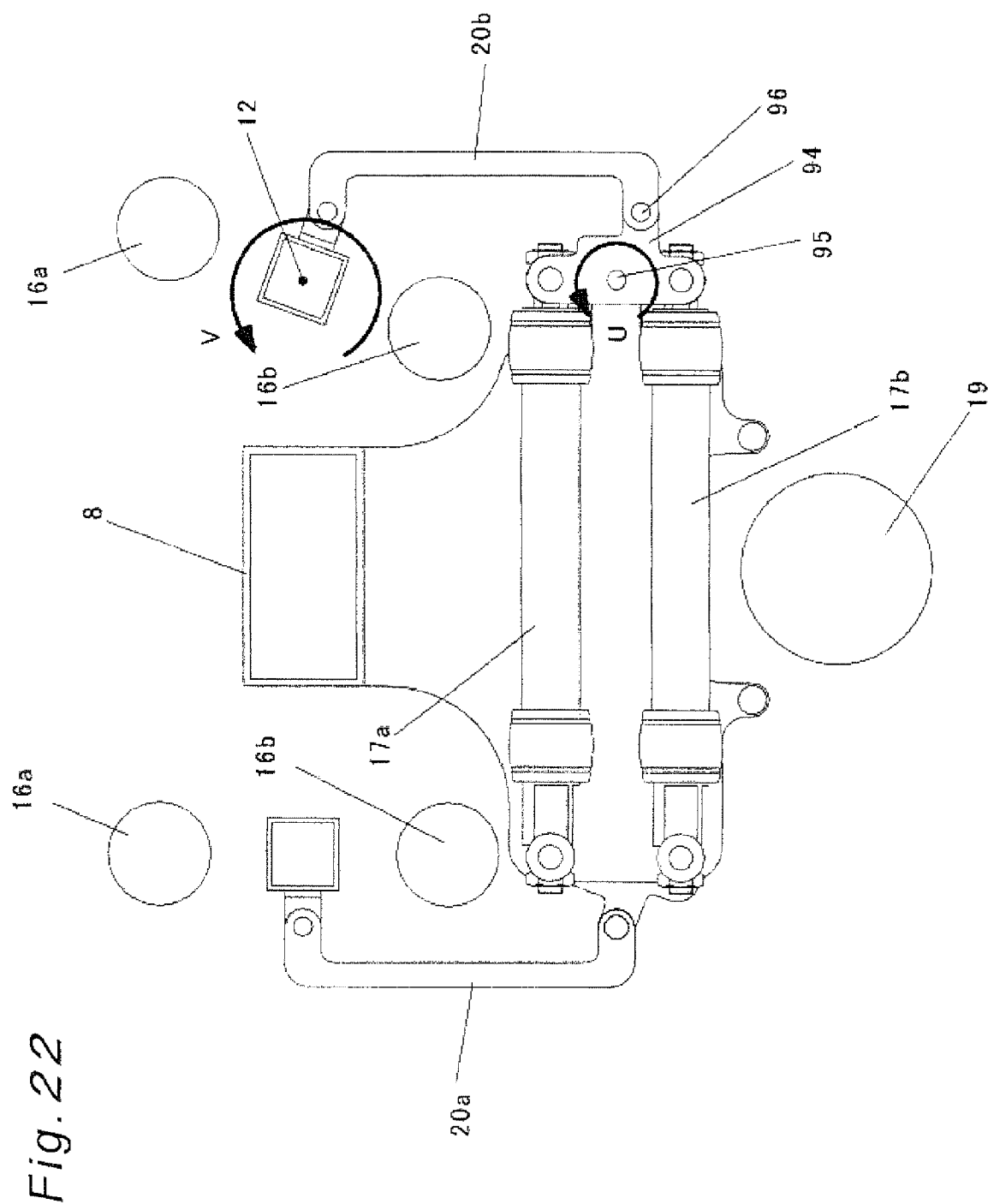
FIG. 22 is a cross-sectional view for explaining a mechanism for driving a first joint of the arm of the robot according to the embodiment of the present invention.

Moreover, with respect to the rotation movements around the first joint axis 12 of the first joint 9, the rotation movements caused by balancing driving operations between the pneumatic artificial muscles 17*a* of the upper portion on the front side and the lower portion on the rear side and the pneumatic artificial muscles 17*b* of the lower portion on the front side and the upper portion on the rear side, are transmitted by a coupling member 20 and driven. Referring to FIG. 22, the above-mentioned method for driving the first joint 9 will be described in detail by exemplifying the case of the right arm 3*b*. FIG. 22 is an A-A line cross-sectional view of FIG. 3. The end portions of the pneumatic artificial muscles 17*a* and 17*b* are coupled to a rocking link 94, and the rocking link 94 is rotatable around the rotation axis 95 of the rocking link. When the pneumatic artificial muscle 17*a* is contracted and the pneumatic artificial muscle 17*b* is expanded, the rocking link 94 generates a rotation movement indicated by an arrow U, and since the rocking link 94 is connected to a coupling member 20*b* on the coupling axis 96, the rotation movement of the rocking link 94 is transmitted so that the right arm 3*b* is driven to exert a rotation movement around the first joint 9 indicated by an arrow V. In the same manner, in the case of the left arm 3*a*, a coupling member 20*a* is driven by the pneumatic artificial muscles 17*a* and 17*b* disposed below so that the first joint is driven.

Figure 4:
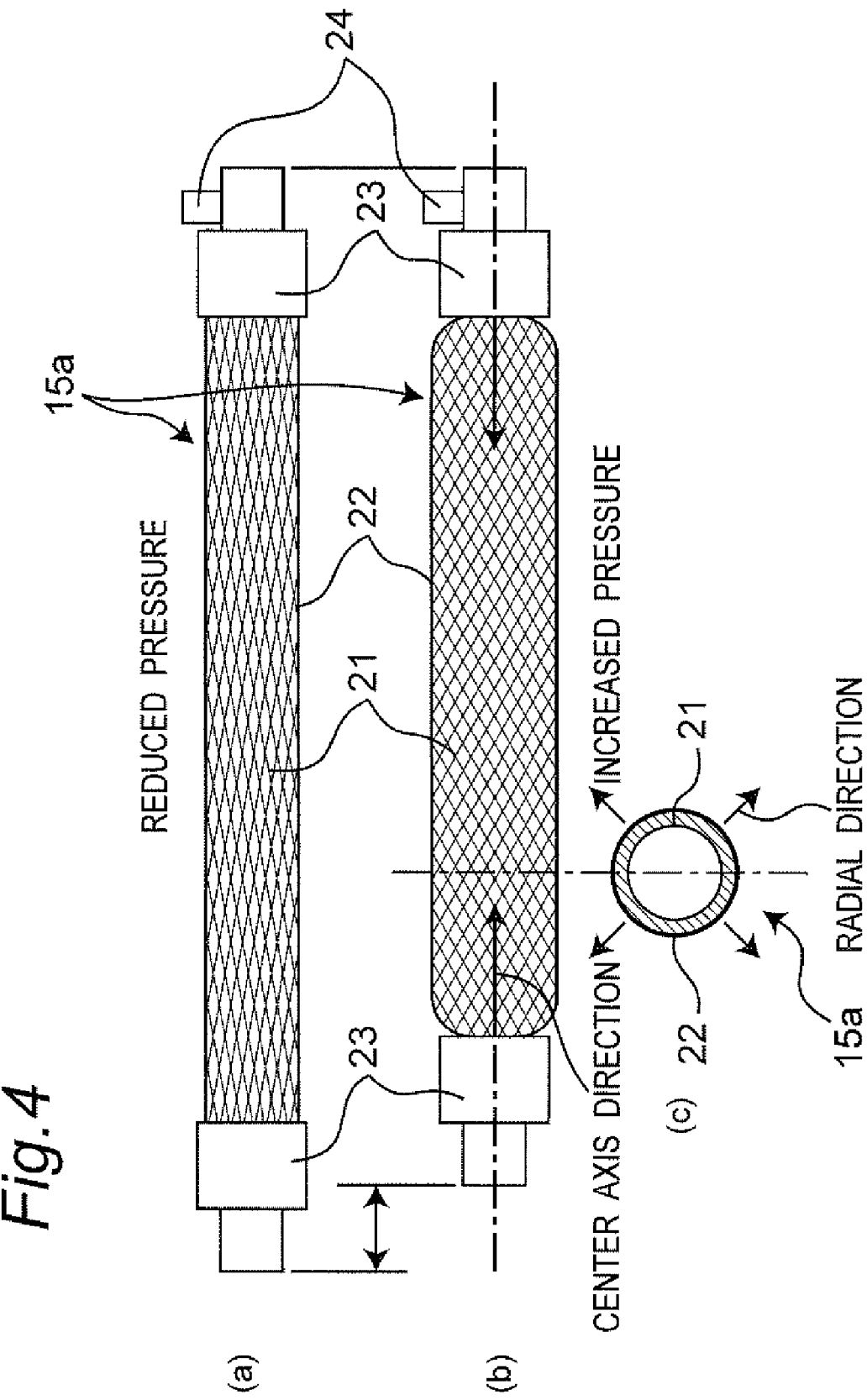
FIG. 4 is a view for explaining a structure of a pneumatic artificial muscle for the robot according to the embodiment of the present invention.

FIGS. 4(*a*), 4(*b*), and 4(*c*) are views each showing the structure of the pneumatic artificial muscle 15*a* shown in FIG. 2. FIG. 4(*a*) is a front view showing a reduced-pressure state of the pneumatic artificial muscle 15*a*, FIG. 4(*b*) is a front view showing a pressurized state of the pneumatic artificial muscle 15*a*, and FIG. 4(*c*) is a cross-sectional view of the pneumatic artificial muscle 15*a*. Since the other pneumatic artificial muscles 15*b*, 15*c*, 15*d*, 16*a*, 16*b*, 17*a*, 17*b*, 17*c*, 17*d*, as well as 18*a*, 18*b*, 18*c*, 18*d*, 18*e*, 18*f*, and 19, which will be described later, have the same structure, the following explanation will be given by typically exemplifying the pneumatic artificial muscle 15*a*. As shown in FIG. 4, the pneumatic artificial muscle 15*a* has a structure in which, on an outer surface of a tube-shaped elastic member 21 formed by a rubber member, a constraint member 22 formed by knitting fiber cords of resin or metal that is a hardly expandable material into a network form, is disposed, with the two end portions of the tube-shaped elastic member 21 being airtightly sealed by sealing members 23. When an inner pressure is given to the inner space of the tube-shaped elastic member 21 by supplying a compressible fluid, such as air, into the tube-shaped elastic member 21 through a fluid inlet-outlet member 14, the tube-shaped elastic member 21 tends to expand mainly in radial directions. However, this expanding movement is converted into a contracting movement in center axis directions of the tube-shaped elastic member 21 by the function of the constraint member 22 so that the overall length is contracted. Since the pneumatic artificial muscle 15*a* is mainly composed of the elastic member, it is possible to provide a safe and light weighted actuator having flexibility.

Figure 5:
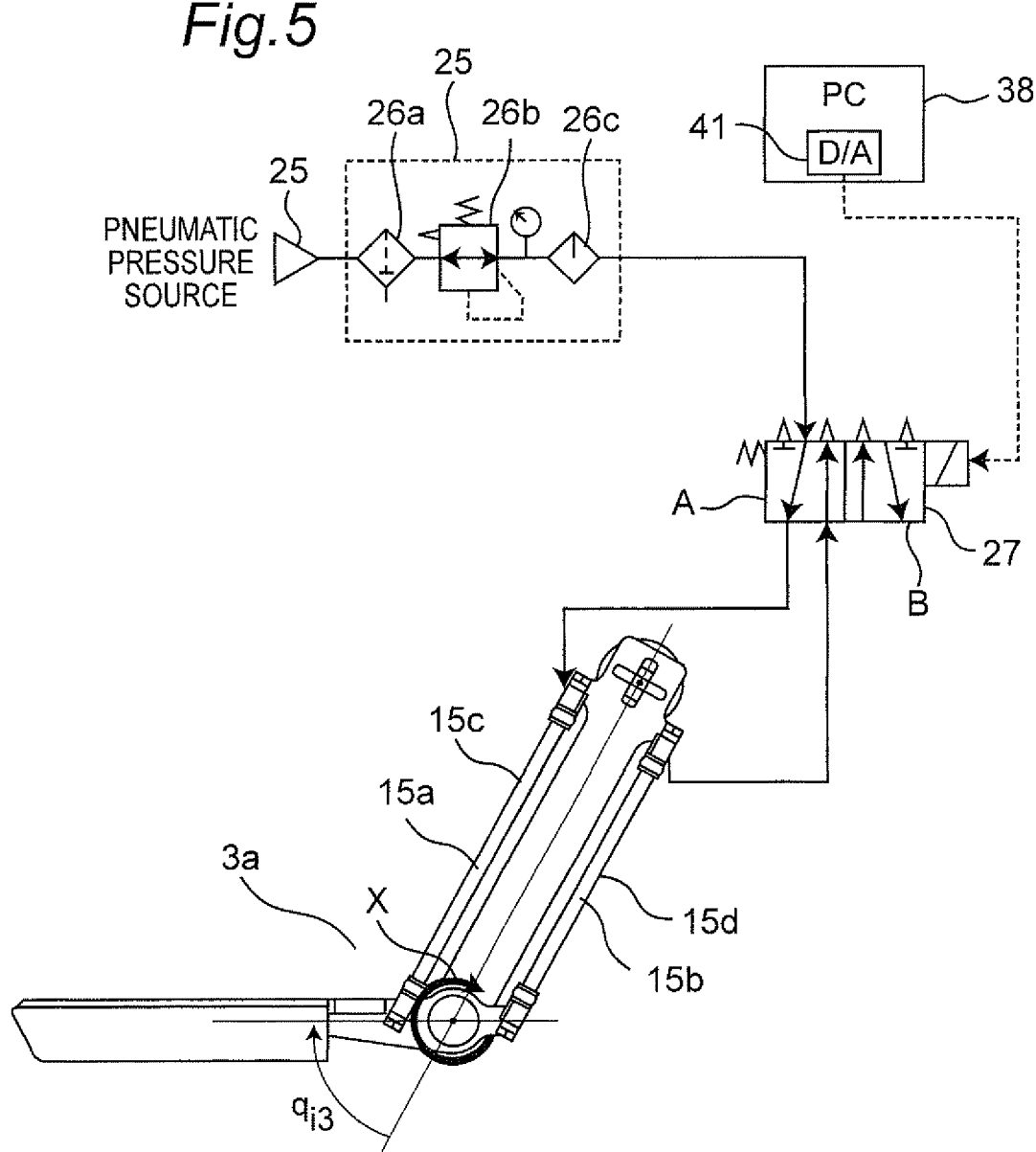
FIG. 5 is a view that shows a structure of a pneumatic pressure supply driving system for driving the pneumatic artificial muscle.

FIG. 5 is a view that shows a structure of an air-pressure supply driving system for driving the pneumatic artificial muscle 15*a*. FIG. 5 illustrates by extracting only the air-pressure supply driving system for driving the third joint 11 of the left arm 3*a*. In FIG. 5, symbol 25 represents an air-pressure source such as a compressor, and symbol 26 represents an air-pressure adjusting unit having one set of a pneumatic filter 26*a*, an air-pressure reducing valve 26*b*, and a lubricator 26*c* for air pressure.

Symbol 27 represents a flow-rate controlling electromagnetic valve with 5 ports that controls the flow rate by driving a spool valve or the like with use of, for example, an electromagnet force. Symbol 38 represents a control apparatus formed by, for example, a general-use personal computer, and a D/A board 41 is installed therein so that, by outputting a voltage instruction value to the flow-rate controlling electromagnetic valve 27 with 5 ports, the flow rates of respective air flows that pass through the fluid inlet/outlet members 24*a* and 24*b* can be controlled. The control apparatus 38 will be described later in detail.

In accordance with the air-pressure supply driving system shown in FIG. 5, a high pressure air generated by the air-pressure source 25 is pressure-reduced by the air-pressure adjusting unit 26 so as to be adjusted to a constant pressure of, for example, 600 kPa, and is supplied to the flow-rate controlling electromagnetic valve 27 with 5 ports. The degree of opening of the flow-rate controlling electromagnetic valve 27 with 5 ports is controlled in proportion to a voltage instruction value outputted from the control apparatus 38 through the D/A board 41. The fluid inlet-outlet members 24 of the tube-shaped elastic members 21, respectively formed by the pair of pneumatic artificial muscles 15*a* and 15*b* and the pair of pneumatic artificial muscles 15*c* and 15*d*, are connected to the flow-rate controlling electromagnetic valve 27 with 5 ports. The paired pneumatic artificial muscles 15*a*, 15*b* and the paired pneumatic artificial muscles 15*c*, 15*d* are disposed substantially in parallel with each other in a longitudinal direction of the first link 6, with end portions on the fluid inlet-outlet member 24 side of the respective tube-shaped elastic members 21 being secured to the end portions of the first link 6 on the second joint 10 side. The other end portions of the respective tube-shaped elastic members 21 of the paired pneumatic artificial muscles 15*a*, 15*b* and the paired pneumatic artificial muscles 15*c*, 15*d* are supported on the second link 7 so as to freely rotate thereon. In FIG. 5 the pneumatic artificial muscles 15*b* and 15*d* are not illustrated because they are respectively placed at positions behind the pneumatic artificial muscles 15*a* and 15*c*. Therefore, as will be described below, the respective tube-shaped elastic members 21 of the paired pneumatic artificial muscles 15a, 15b and the paired pneumatic artificial muscles 15c, 15d are expanded and contracted so that the second link 7 is driven to forwardly/reversely rotate around the third joint axis 14 of the third joint 11. In this case, in FIG. 5, a rightward rotation indicated by an arrow X is defined as a forward direction, and a leftward rotation that is reversed to the arrow X is defined as a reverse direction.

Figure 6C:
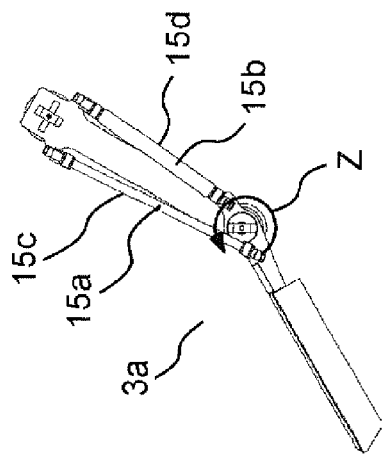
FIG. 6C is a view that shows still other operations of the third joint of the left arm of the robot according to the embodiment of the present invention.
Figure 6B:
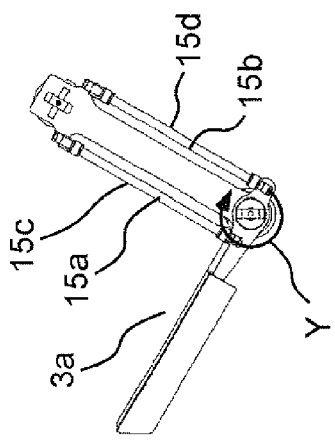
FIG. 6B is a view that shows other operations of the third joint of the left arm of the robot according to the embodiment of the present invention.
Figure 6A:
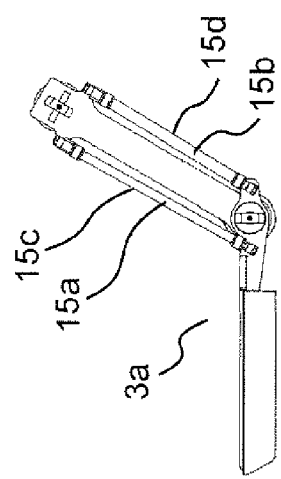
FIG. 6A is a view that shows operations of a third joint of a left arm of the robot according to the embodiment of the present invention.

In a case where a positive voltage instruction value outputted by the control apparatus 38 is inputted to the flow-rate controlling electromagnetic valve 27 with 5 ports from the D/A board 41, a state indicated by pneumatic circuit symbol A of FIG. 5 is brought about in which a passage from the air-pressure source 25 side toward the fluid inlet-outlet member 24 side of the tube-shaped elastic members 21 of the pneumatic artificial muscles 15a and 15b is opened through the flow-rate controlling electromagnetic valve 27 with 5 ports so that an air flow having a flow rate in proportion to the absolute value of the voltage instruction value is supplied to each of the pneumatic artificial muscles 15a and 15b. Moreover, on the pneumatic artificial muscles 15c, 15d side, a passage from each of the fluid inlet-outlet members 24 of the tube-shaped elastic members 21 toward an atmospheric pressure side is opened through the flow-rate controlling electromagnetic valve 27 with 5 ports so that an air flow having a flow rate in proportion to the absolute value of the voltage instruction value is exhausted into the atmosphere from each of the pneumatic artificial muscles 15c and 15d. Therefore, the overall length of each of the pneumatic artificial muscles 15a and 15b is contracted, while the overall length of each of the pneumatic artificial muscles 15c and 15d is expanded, so that the third joint 11 carries out a rightward rotation movement indicated by an arrow Y around the third joint axis 14 from the state shown in FIG. 6A to the state shown in FIG. 6B, at a speed in proportion to the absolute value of the voltage instruction value.

On the other hand, in a case where a negative voltage instruction value outputted from the control apparatus 38 is inputted to the flow-rate controlling electromagnetic valve 27 with 5 ports from the D/A board 41, the flow-rate controlling electromagnetic valve 27 with 5 ports is switched to the state indicated by pneumatic circuit symbol B so that the movements of the pneumatic artificial muscles 15a, 15b and the pneumatic artificial muscles 15c, 15d are reversed from each other. Thus, the third joint 11 carries out a leftward rotation movement around the third joint axis 14. That is, a passage from the air-pressure source 25 side toward the fluid inlet-outlet member 24 side of each of the tube-shaped elastic members 21 of the pneumatic artificial muscles 15c and 15d is opened through the flow-rate controlling electromagnetic valve 27 with 5 ports so that an air flow having a flow rate in proportion to the absolute value of the voltage instruction value is supplied to each of the pneumatic artificial muscles 15c and 15d. Moreover, on the pneumatic artificial muscles 15a, 15b side, a passage from each of the fluid inlet-outlet members 24 of the tube-shaped elastic members 21 toward the atmospheric pressure side is opened through the flow-rate controlling electromagnetic valve 27 with 5 ports so that an air flow having a flow rate in proportion to the absolute value of the voltage instruction value is exhausted into the atmosphere from each of the pneumatic artificial muscles 15a and 15b. Therefore, the overall length of each of the pneumatic artificial muscles 15c and 15d is contracted, while the overall length of each of the pneumatic artificial muscles 15a and 15b is expanded, so that the third joint 11 carries out a leftward rotation movement as indicated by an arrow Z around the third joint axis 14 from the state shown in FIG. 6A to the state shown in FIG. 6C, at a speed in proportion to the absolute value of the voltage instruction value.

As described above, the second link 7 is driven to carry out forward/reverse rotation movements by the pneumatic artificial muscles 15a, 15b and the pneumatic artificial muscles 15c, 15d so that the first link 6 and the second link 7 are driven to carry out rocking movements, that is, rotation movements at an angle $q_{L3}$.

On the respective joints 9, 10, and 11 of the arm 3, joint lock mechanisms 28a, 28b, 28c, 28d, 28e, and 28f to be used for securing the joints 9, 10, and 11 are respectively placed on the first joint 9 of the left arm 3a, the second joint 10 of the left arm 3a, the third joint 11 of the left arm 3a, the first joint 9 of the right arm 3b, the second joint 10 of the right arm 3b, and the third joint 11 of the right arm 3b. Since the respective joint lock mechanisms 28a, 28b, 28c, 28d, 28e, and 28f have the same structure, the following description will discuss the joint lock mechanism 28 as a typical example, when the structures and the like of the respective joint lock mechanisms 28a, 28b, 28c, 28d, 28e, and 28f are explained.

Figure 7A:
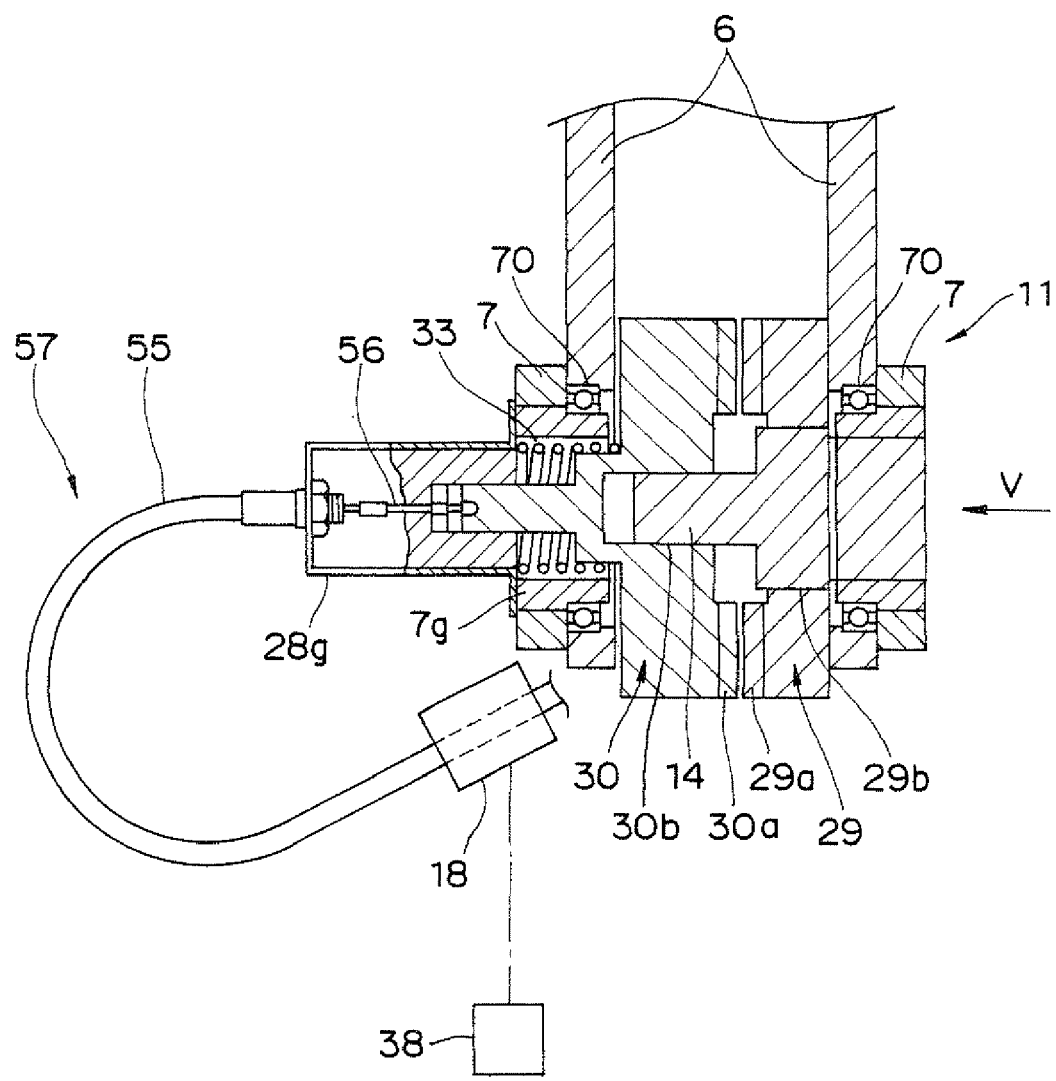
FIG. 7A is a cross-sectional view taken along a joint axis to show a structure of a joint lock mechanism of the robot according to the embodiment of the present invention.
Figure 7B:
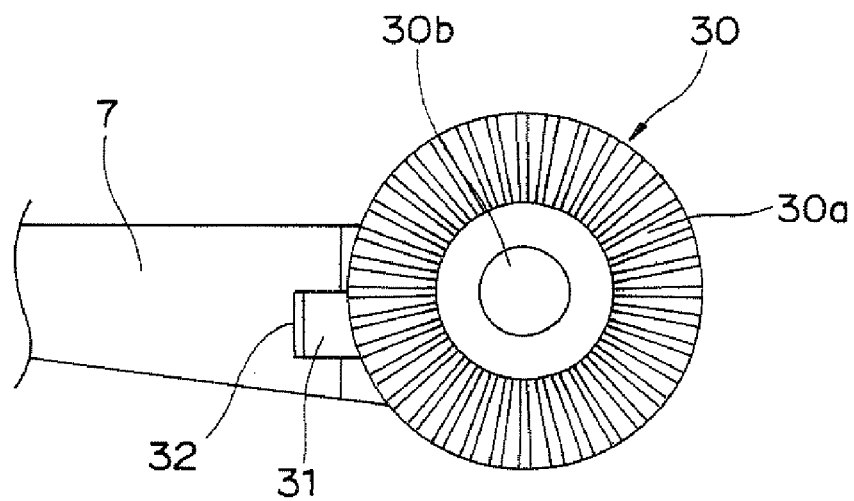
FIG. 7B is a view showing the structure of the joint lock mechanism seen in an arrow V direction of FIG. 7A.
Figure 7C:
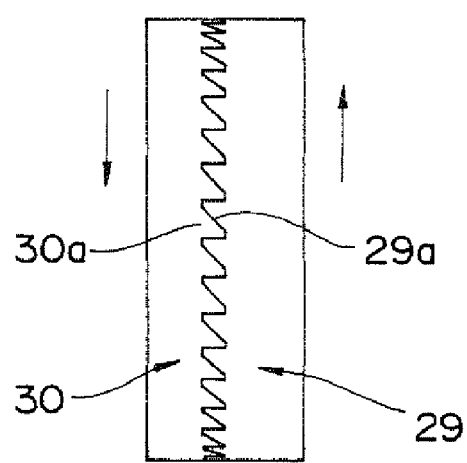
FIG. 7C is an outer side view of an opposing gear in the structure of the joint lock mechanism.

FIGS. 7A to 7C show the joint lock mechanism 28 in detail. FIG. 7A is a cross-sectional view passing through the joint axis. FIG. 7B is a view seen in a direction of an arrow V of FIG. 7A, that is, when a surface on which a gear portion of one of opposing gears is formed is seen in an axis direction of the joint axis. FIG. 7C is an outer side view of the two opposing gears.

Figure 8:
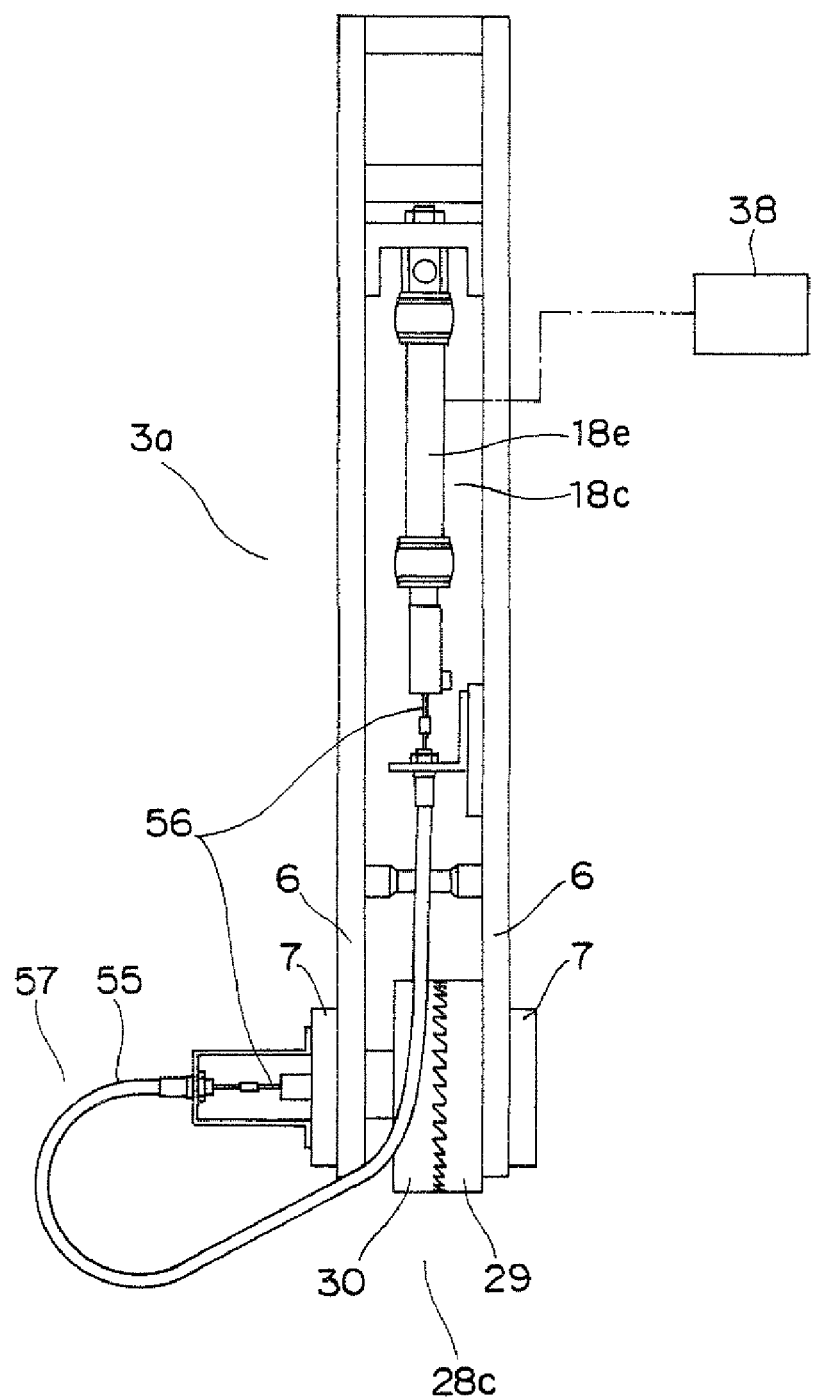
FIG. 8 is a view for explaining a driving mechanism of the joint lock mechanism of the robot according to the embodiment of the present invention.

Moreover, FIG. 8 shows a driving mechanism of the joint lock mechanism 28 in detail. FIG. 8 is a view in which the first link 6 of the left arm 3a is seen in a direction of arrow W shown in FIG. 3. The first link 6 of the right arm 3b has a laterally symmetrical structure with respect to the structure shown in FIG. 8.

In FIG. 8, Symbol 29 represents a disc-shaped fixed opposing gear having an annular gear portion 29a on the opposed surface, and a round hole 29b to which the joint axis of a joint to be subjected to a locking and lock-releasing operations is inserted and fitted so as not to be rotated is formed in a center thereof, and the fixed opposing gear is secured so as not to be moved relatively to, out of structural members connected by the joint, the structural member as well as to the joint axis closer to the base unit 1. For example, in the case of the joint lock mechanism 28c of the third joint 11, the fixed opposing gear 29 is secured to the first link 6 and the third joint axis 14 serving as examples of the structural member and the joint axis closer to the base unit 1 so that the tip of the third joint axis 14 of the third joint 11 is allowed to pass through the hole 29b of the fixed opposing gear 29, and is inserted and fitted thereto so as not to be rotated relatively. That is, the third joint axis 14 and the fixed opposing gear 29 are secured integrally. The first link 6 and the second link 7 are coupled to each other by a bearing 70 in the third joint 11 so as to be rotatable relative to each other. Symbol 7g represents a collar that is integrally rotatable with the second link 7 and is relatively rotatable with respect to the first link 6 by the bearing 70, and symbol 28g represents a casing in which a pressing spring 33 and the like, which will be described later, are disposed.

Symbol 30 represents a disc-shaped movable opposing gear that has an annular gear portion 30a formed on the opposed surface, and can be meshed with the gear portion 29a of the fixed opposing gear 29, and a round concave portion 30b that can communicate with the hole 29b is formed in a center thereof, and the joint axis (for example, the tip of the third joint axis 14 in the case of the joint lock mechanism 28c of the third joint 11) is disposed in the concave portion 30b so as to be opposed to the fixed opposing gear 29 in a manner to be inserted therein so as to be relatively rotatable therein and shiftable in the axis direction. The movable opposing gear is not secured to the joint axis, and is allowed to carry out a translation movement in the axis direction of the joint axis, and also to rotate around the rotation axis. Moreover, a guide protrusion 31 that protrudes in a radial direction is provided at one portion on the outer circumferential surface of the movable opposing gear 30 so that, out of the structural members to be connected by the joint, the guide protrusion 31 is meshed with a guide groove 32 provided in the structural member closer to the tip unit. For example, in the case of the joint lock mechanism 28c of the third joint 11, the guide groove 32 is formed in the second link 7 (see FIG. 7B). The guide protrusion 31 can make a translation movement relatively along the longitudinal direction in a drawing-surface penetrating direction of FIG. 75, that is, in a thickness direction of the movable opposing gear 30) of the guide groove 32 with respect to the guide groove 32. In other words, the movable opposing gear 30 and the structural member closer to the tip unit (in the above case, the second link 7) can make translation movements relatively in the center axis direction of the joint axis (in the above case, the third joint axis 14). However, with respect to the rotation movement around the center axis of the joint axis, the movable opposing gear 30 and the structural member closer to the tip unit (in the above case, the second link 7) carry out rotation movements integrally, due to a constraint between the guide protrusion 31 and the guide groove 32 meshed with each other. FIG. 7A shows a state in which the meshed state between the guide protrusion 31 and the guide groove 32 is released.

The gear portion 29a on the opposed surface of the fixed opposing gear 29 and the gear portion 30a on the opposed surface of the movable opposing gear 30 have serrated shapes in cross section respectively, and by a pressing force of a pressing spring 33 placed inside the collar 7g of the casing 28g, exerted in a center axis direction of the movable opposing gear 30 toward the opposite side to the fixed opposing gear 29 in the movable opposing gear 30, the fixed opposing gear 29 and the movable opposing gear 30 are pressed to be meshed with each other so that functions of the opposing gears 29 and 30 are exerted. In the case where the gear portion 29a of the fixed opposing gear 29 and the gear portion 30a of the movable opposing gear 30 are meshed with each other, with respect to rotation movements around the joint axis of the fixed opposing gear 29 and the movable opposing gear 30, the rotation in a rotation direction (the direction indicated by an arrow in FIG. 7C) that causes contact between the mutual vertical surfaces of the respective teeth of the gear portion 29a and the gear portion 30a (mutual upright surfaces in the thickness directions of the opposing gears 29 and 30) is prevented so as to be fixed. In this case, since the structural member (the first link 6 in the above case) closer to the base unit 1 is secured to the fixed opposing gear 29, with the structural member (the second link 7 in the above case) closer to the tip unit being secured to the movable opposing gear 30 through the guide protrusion 31 and the guide groove 32, the joint (the third joint 11 in the above case) is locked so that no relative rotation movements between the two structural members (the first link 6 and the second link 7 in the above case) is generated. In contrast, a rotation direction (a direction opposite to the direction of the arrow in FIG. 7C) that causes contact between the mutual slanting surfaces of the respective teeth of the gear portion 29a and the gear portion 30a (mutual slanting surfaces in a slanting direction relative to the thickness directions of the opposing gears 29 and 30) rises along the slanting surfaces. Therefore, relative rotation movements between the two structural members (the first link 6 and the second link 7 in the above case) are enabled. As a result, the joint lock mechanism 28 functions as a one-way clutch.

The movable opposing gear 30 is connected to the pneumatic artificial muscle 18 for driving the joint lock mechanism (more specifically, the pneumatic artificial muscles 18a, 18b, 18c, 18d, 18e, and 18f, indicated by 18 as a typical example upon explaining the structure) through a control cable 57 that is composed of an outside guide tube 55 and a pulling wire 56. FIG. 7A shows a state in which the meshed state between the guide protrusion 31 and the guide groove 32 is released, and this state indicates that, by the driving operation of the pneumatic artificial muscle 18, the movable opposing gear 30 is moved by the pulling wire 56 in the center axis direction so as to depart from the fixed opposing gear 29 (left side in FIG. 7A) so that the gear portion 29a and the gear portion 30a are separated from each other. In contrast, when the movable opposing gear 30 is moved by the pulling wire 56 in the center axis direction by the driving operation of the pneumatic artificial muscle 18 so as to come closer to the fixed opposing gear 29 (right side in FIG. 7A), the gear portion 29a and the gear portion 30a is brought into a meshed state. Among the pneumatic artificial muscles 18 for driving the joint lock mechanism, the pneumatic artificial muscle 18a (illustrated in FIG. 3) is placed on the base unit 1 and drives the joint rock mechanism 28a of the first joint 9 of the left arm 3a. The pneumatic artificial muscle 18b (disposed behind the pneumatic artificial muscle 18a in FIG. 3) is disposed on the base unit 1 and drives the joint rock mechanism 28b of the first joint 9 of the right arm 3b. The pneumatic artificial muscle 18c (disposed behind the pneumatic artificial muscle 18e in FIG. 8) is disposed inside the first link 6 of the left arm 3a and drives the joint rock mechanism 28c of the second joint 10 of the left arm 3a. The pneumatic artificial muscle 18d (disposed in the right arm 3b in the same manner as in the pneumatic artificial muscle 18c in FIG. 8) is disposed inside the first link 6 of the right arm 3b and drives the joint rock mechanism 28d of the second joint 10 of the right arm 3b. The pneumatic artificial muscle 18e (illustrated in FIG. 8) is disposed inside the first link 6 of the left arm 3a, and drives the joint rock mechanism 28e of the third joint 11 of the left arm 3a. The pneumatic artificial muscle 18f (disposed in the right arm 3b in the same manner as in the pneumatic artificial muscle 18e in FIG. 8) is disposed inside the first link 6 of the right arm 3b and drives the joint rock mechanism 28f of the third joint 11 of the right arm 3b.

When a high-pressure air is supplied to the pneumatic artificial muscle 18 so that the pneumatic artificial muscle 18 is contracted, the movable opposing gear 30 is pulled by the pulling wire 56 of the control cable 57 coupled to the pneumatic artificial muscle 18 so that, against the pressing force of the pressing spring 33 of the joint lock mechanism 28, the gear 30 is moved so as to depart from the fixed opposing gear 29 in the center axis direction and the meshed state between the mutual gear portion 29a and gear portion 30a of the opposing gears 29 and 30 is released. In contrast, when a high-pressure air is discharged from the pneumatic artificial muscle 18 so that the pneumatic artificial muscle 18 is expanded, the pulling force applied to the movable opposing gear 30 by the pulling wire 56 of the control cable 57 is released so that the mutual gear portion 29a and gear portion 30a of the opposing gears 29 and 30 are meshed with each other by the pressing force of the pressing spring 33 of the joint lock mechanism 28, and the joint is consequently locked so as not to be relatively rotatable.

With respect to the layout direction of the joint lock mechanism 28 in each of the joints of the left arm 3a and the right arm 3b, the joint lock mechanism 28 is disposed so that the rotatable direction as one-way clutch corresponds to a rotation direction indicated by an arrow R in FIGS. 2 and 3, while the locking direction (direction in which no relative rotations are available) corresponds to a rotation direction reversed to the arrow R in the figure. By setting this layout direction, the joint lock is allowed to function when a person to be cared or a transporting object is placed on the arms 3 so that, since the load given by the weight of the person to be cared or the transporting object is supported by the joint lock mechanism 28, the person to be cared or the transporting object can be held more easily and stably with high reliability.

Figure 9A:
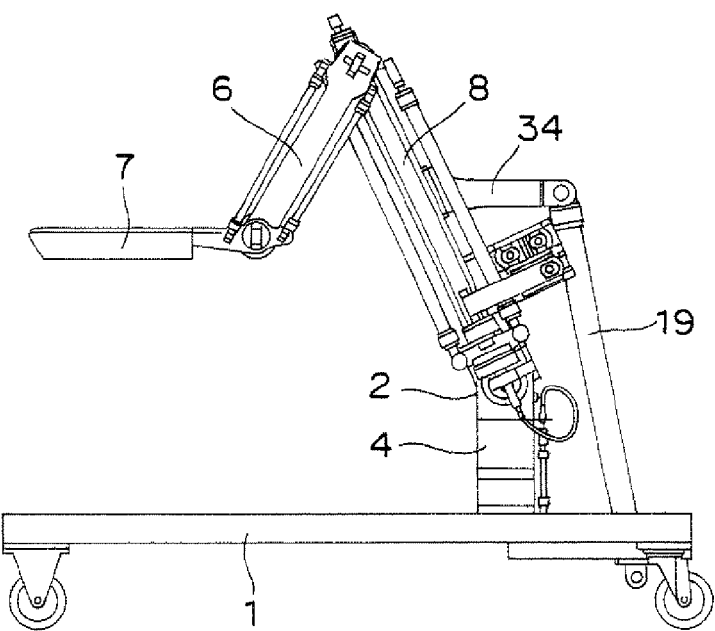
FIG. 9A is a view for explaining operations of a waist mechanism of the robot according to the embodiment of the present invention.
Figure 9B:
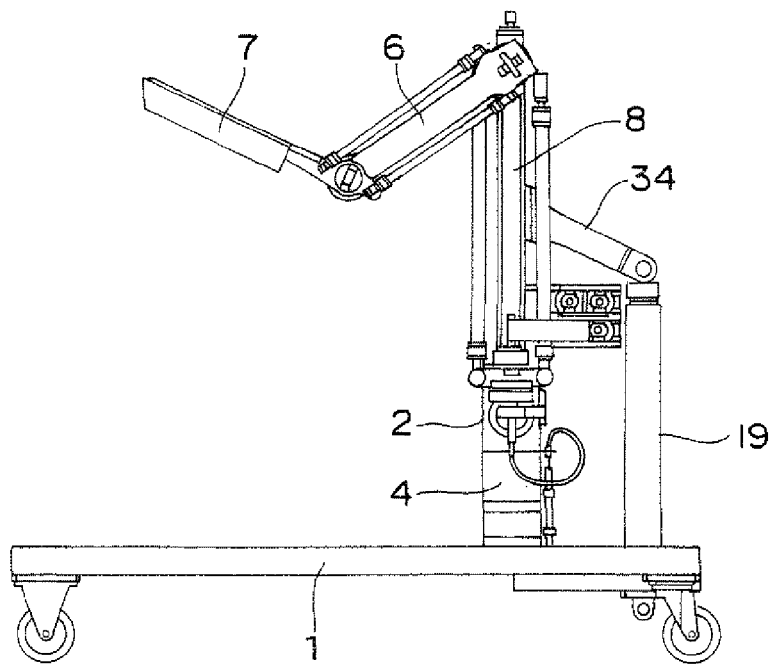
FIG. 9B is a view for explaining other operations of the waist mechanism of the robot according to the embodiment of the present invention.

Referring to FIG. 3, FIG. 9A, and FIG. 9B, the following description will discuss the waist mechanism 2. The waist mechanism 2 is driven by the pneumatic artificial muscle 19. The pneumatic artificial muscle 19 has one end secured onto the base unit 1 so as to freely rotate thereon, with the other end being secured onto the rear end of a force transmission lever 34 so as to freely rotate thereon. The front end of the force transmission lever 34 is secured onto the body unit 8. By supplying high-pressure air to the pneumatic artificial muscles 19 so that the pneumatic artificial muscles 19 are contracted, the force transmission lever 34 is pulled rearward, and the body unit 8 carries out a pivotal movement around the joint axis 2A of the waist mechanism 2 so that the body unit 8 is raised from a forward tilted state shown in FIG. 9A to an upright state shown in FIG. 9B. In contrast, when high-pressure air is discharged from the pneumatic artificial muscles 19 so that the pneumatic artificial muscles 19 are expanded, the body unit 8 is tilted by the weight of the body unit 8 or the arm 3 forward from the upright state shown in FIG. 9B to the forward tilted state shown in FIG. 9A.

Figure 10:
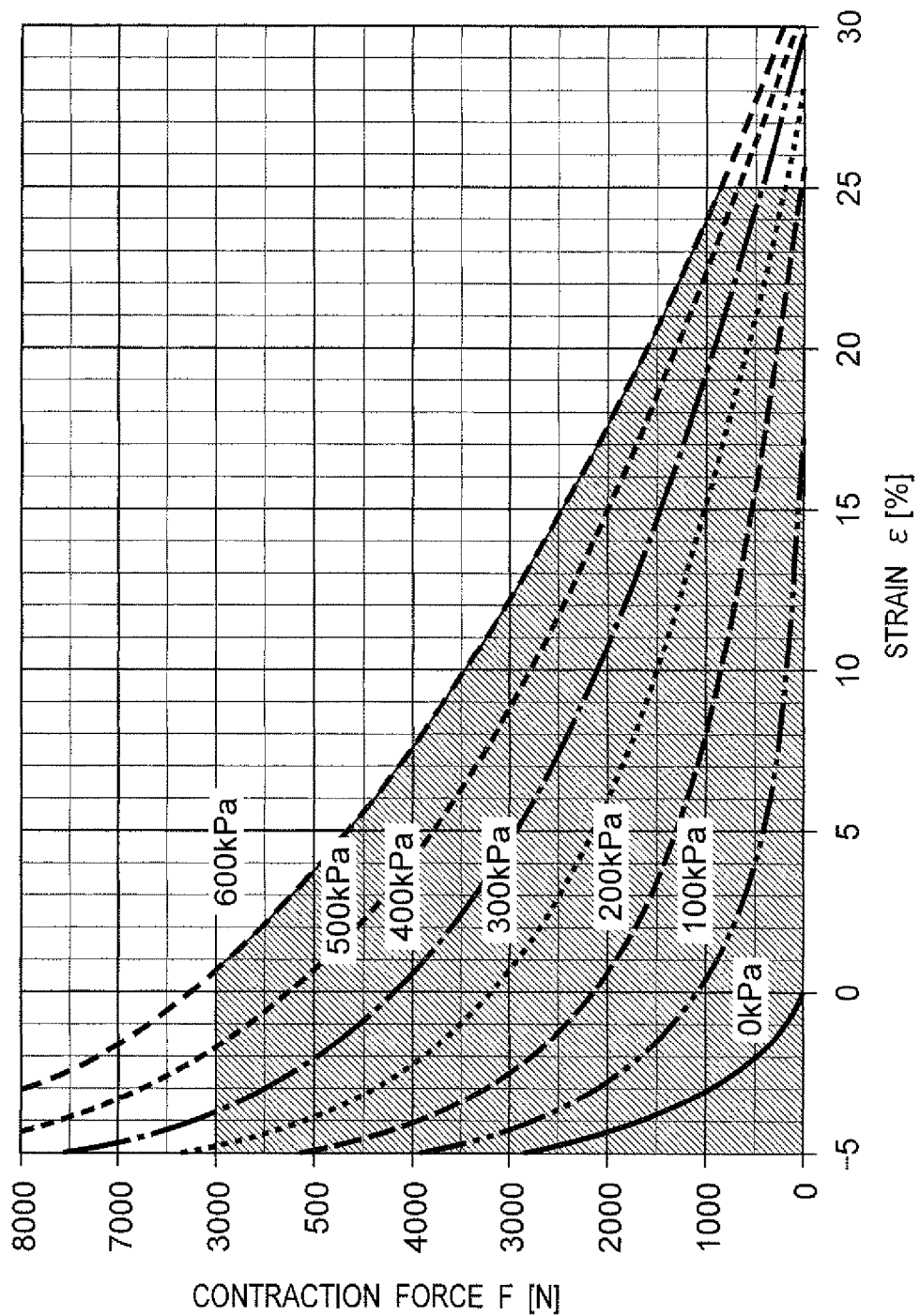
FIG. 10 is a characteristic view of the pneumatic artificial muscle of the robot according to the embodiment of the present invention.

A pressure sensor 67 (see FIG. 3) connected to the control apparatus 38 is provided to each pneumatic artificial muscle 19 that drives the waist mechanism 2 so that it is possible to measure the inner pressure of the pneumatic artificial muscle 19 by the pressure sensor 67. In accordance with an inner pressure $P_p$ of the pneumatic artificial muscle 19 obtained by the pressure sensor 67 and a strain $\epsilon$ in the pneumatic artificial muscle 19 obtained from angle information of the encoder 37 of the joint axis 2A of the waist mechanism 2, operation mode switching means 47 can determine whether or not the robot is in a state of lifting a load such as a heavy object or the like. Among the inner pressure $P_p$, the strain $\epsilon$, and the contracting force F of the pneumatic artificial muscle 19, there is a relationship as shown in FIG. 10. By utilizing this characteristic, the contracting force F can be calculated by contracting force calculation means 194 based upon the inner pressure $P_p$ and the strain $\epsilon$ of the pneumatic artificial muscle 19. When the contracting force $F_p$ thus calculated is greater than the value of the contracting force in a state in which the robot is not lifting a load such as a heavy object, the operation mode switching means 47 can determine that the robot is lifting a load such as a heavy object.

The determination information as to whether or not the robot is lifting the load such as a heavy object is obtained by the operation mode switching means 47, which will be described later, and the determination result is outputted to joint lock mechanism control means 59, which will be described later.

Figure 11A:
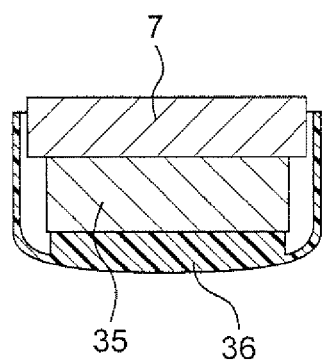
FIG. 11A is a cross-sectional front view for explaining a layout of a force sensor in a second link of the robot according to the embodiment of the present invention.
Figure 11B:
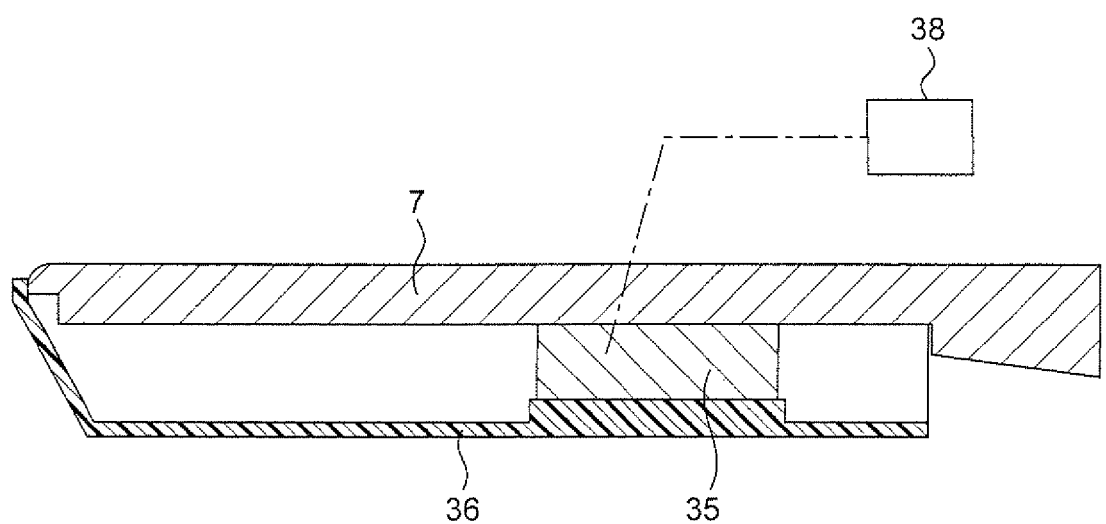
FIG. 11B is a cross-sectional side view for explaining the layout of the force sensor in the second link of the robot according to the embodiment of the present invention.

As shown in FIG. 11A and FIG. 11B, three-axes force sensor 35, which functions as one example of an external force detection device and can detect translation forces in three directions, is disposed near the center portion of the second link 7 of the arm 3. A force detection external cover 36 is placed on the force sensor 35 with a clearance so as not to be made in contact with the structural member of the second link 7, and the force sensor 35 detects a force exerted between the force detection external cover 36 and the second link 7 of the arm 3, and outputs the detected force to the control apparatus 38. The force detection external cover 36 has such a structure as to cover substantially a half of the external surface of the cross section in the width direction of the second link 7 and most of portions of the second link 7 in the link longitudinal direction, so that it is possible to detect a force exerted on the second link 7 at most of the portions of the surface of the second link 7. Moreover, the force sensor 35 is disposed to be positioned below the arm 3 in a basic transporting orientation as shown in FIGS. 2 and 3 so that, even in a case where a person to be cared or a transporting object is placed on the upper surface of the arm 3, the person to be cared or the transporting object is prevented from being made in contact with the force sensor 35. Thus, it is possible to detect an external force by the force sensor 35, without being influenced by the person to be cared or the transporting object.

The control apparatus 38 shown in FIGS. 1, 5, and the like, is composed of a general-use personal computer as hardware, and portions thereof except for an input/output IF 40 are achieved by a control program 39 as software, which is executed by the personal computer.

The input/output IF 40 is composed of the D/A board 41, an A/D board 42, and a counter board 43 that are connected to an extension throttle such as a PCI bus of the personal computer.

The control apparatus 38 is allowed to function by executing the control program 39 for controlling the operations of the robot, and pieces of joint angle information, outputted from the encoders 37 of the respective joints 9, 10, and 11 of the left arm 3a and the right arm 3b, are received by the control apparatus 38 through the counter board 43, while pieces of external force information detected by the force sensors 35 disposed on the left arm 3a and the right arm 3b are received by the control apparatus 38 through the A/D board 42, so that control instruction values for use in rotation movements of the respective joints are calculated by the control apparatus 38. The respective control instruction values thus calculated are provided to the flow-rate controlling electromagnetic valve 27 with 5 ports through the D/A board 41 so that the pneumatic artificial muscles 15a, 15b, 15c, 15d, 16a, and 16b of the respective joints 9, 10, and 11 of the arm 3 are driven by the flow-rate controlling electromagnetic valve 27 with 5 ports.

In FIG. 1, symbol 58 represents an operation mode switches, which is provided with three buttons, namely, an advancing button 64, a retreating button 65, and a stop button 66, and information as to which button has been pressed is inputted to the control apparatus 38 through a digital I/O.

Figure 12:
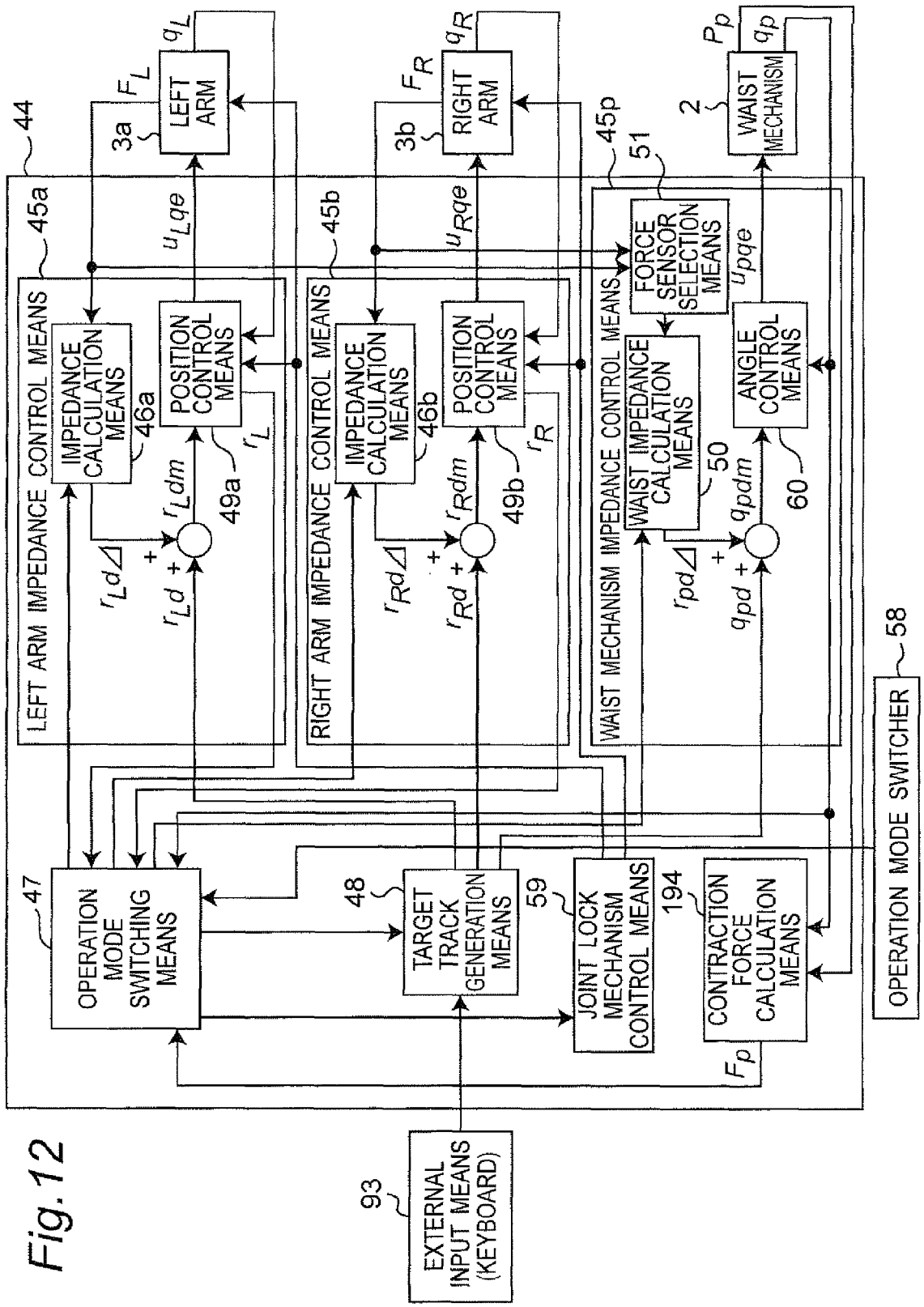
FIG. 12 is a block diagram that shows robot operation control means achieved by a control program that is executed in a control apparatus of the robot according to the embodiment of the present invention.

FIG. 12 is a block line diagram that shows a robot control system achieved by the control program 39 to be executed by the control apparatus 38. In other words, this block diagram shows the structure of the robot operation control means 44 that controls operations of the robot by using the control program 39 based upon the information from the input/output IF 40.

The robot control system is provided with the operation mode switching means 47 and the impedance control means 45.

The impedance control means 45 is composed of left-arm impedance control means 45a, right-arm impedance control means 45b, and waist mechanism impedance control means 45p, and the respective control means control operations of the left arm 3a, the right arm 3b, and the waist mechanism 2 respectively. Since the left-arm impedance control means 45a and the right-arm impedance control means 45b have the same structure and functions, the following explanation will be typically given to the impedance control means 45 in this case. In the following description, a subscript i is given as L or R, and indicates an input/output signal in the left-arm impedance control means 45a or the right-arm impedance control means 45b. For example, the joint angle of the arm 3 represents a joint angle $q_L$ of the left arm 3a corresponding to an input signal to the left-arm impedance control means 45a or a joint angle $q_R$ of the right arm 3b corresponding to an input signal to the right-arm impedance control means 45b. For easier understanding, respectively different left and right characters or numbers are given in parentheses after a representative character or number.

The impedance control means 45 (45a or 45b) is designed to have impedance calculation means 46 (46a or 46b) and position control means 49 (49a or 49b). A force $F_{iL}$ ($F_{LL}$ or $F_{RL}$) measured by the force sensor 35 is inputted to the impedance calculation means 46 (46a or 46b), and a tip-unit target compensating value $r_{id\Delta}$ ($r_{Ld\Delta}$ or $r_{Rd\Delta}$) is outputted from the impedance calculation means 46 (46a or 46b). A value $r_{idm}$ ($r_{Ldm}$ or $r_{Rdm}$) which is obtained in the impedance control means 45 (45a or 45b) by adding the tip-unit target compensating value $r_{id\Delta}$ ($r_{Ld\Delta}$ or $r_{Rd\Delta}$) to a desired position value $r_{id}$ ($r_{Ld}$ or $r_{Rd}$) of the arm 3 (3a or 3b) inputted from target track generation means 48, and a joint angle $q_i$ ($q_L$ or $q_R$) of the arm 3' (3a or 3b), measured by the encoder 37, are respectively inputted to the position control means 49 (49a or 49b), and a joint instruction value $u_{iq}$ ($u_{Lq}$ or $u_{Lq}$) is outputted from the position control means 49 (49a or 49b) so as to form an instruction value to be given to the arm 3 (3a or 3b).

The impedance calculation means 46 (46a or 46b) is a portion to function to allow the arm 3 (3a or 3b) to achieve a mechanical impedance, and based upon impedance parameters of inertia M, viscosity D, elasticity K, a current value $q_i$ ($q_L$ or $q_R$) of the joint angle, and an external force $F_i$ ($F_L$ or $F_R$) detected by the force sensor 35, the impedance calculation means 46 (46a or 46b) calculates a tip-unit desired position compensating output $r_{id\Delta}$ ($r_{Ld\Delta}$ or $r_{Rd\Delta}$) used for allowing the arm 3 (3a or 3b) to achieve a mechanical impedance from the following expression (1), and outputs the resulting value. The tip-unit desired position compensating output $r_{id\Delta}$ ($r_{Ld\Delta}$ or $r_{Rd\Delta}$) is added to the tip-unit desired position value $r_{id}$ ($r_{Ld}$ or $r_{Rd}$) outputted from the target track generation means 48 in the impedance control means 45 (45a or 45b), so that a tip-unit position compensating target vector $r_{idm}$ ($r_{Ldm}$ or $r_{Rdm}$) is generated.

[Formula 1]

$$r_{i\Delta d} = \left(s^2 \hat{M} + s\hat{D} + \hat{K}\right)^{-1} F_i \quad \text{Expression (1)}$$

[Formula 2]

$$\hat{M} = \begin{bmatrix} M & 0 & 0 \\ 0 & M & 0 \\ 0 & 0 & M \end{bmatrix} \quad \text{Expression (2)}$$

[Formula 3]

$$\hat{D} = \begin{bmatrix} D & 0 & 0 \\ 0 & D & 0 \\ 0 & 0 & D \end{bmatrix} \quad \text{Expression (3)}$$

[Formula 4]

$$\hat{K} = \begin{bmatrix} K & 0 & 0 \\ 0 & K & 0 \\ 0 & 0 & K \end{bmatrix} \quad \text{Expression (4)}$$

In these expressions, s represents a Laplace operator. With respect to the impedance parameters of inertia M, viscosity D, and elasticity K, values that provide good operability for the robot are searched in a try-and-error method through experiments, and are respectively determined.

Figure 13:
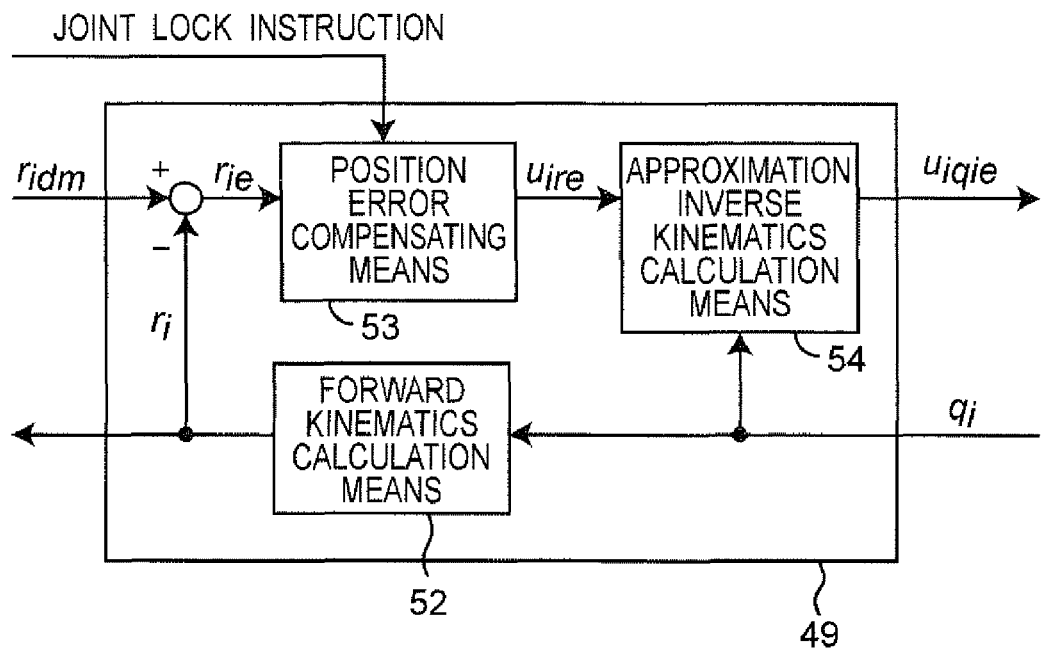
FIG. 13 is a view that shows a detailed structure of position control means of the control apparatus of the robot according to the embodiment of the present invention.

FIG. 13 is a view that shows the position control means 49 (49a or 49b) in detail. Symbol 53 represents position error compensating means, and an error $r_{ie}$ ($r_{Le}$ or $r_{Re}$) between the tip-unit position vector $r_i$ ($r_L$ or $r_R$) calculated by forward kinematics calculation means 52 from the current value $q_i$ ($q_L$, or $q_R$) of the joint angle vector measured in the arm 3 (3a or 3b) and the tip-unit compensation target vector $r_{idm}$ ($r_{Ldm}$, or $r_{Rdm}$) is inputted to the position error compensating means 53, and a position error compensating output $u_{ire}$ ($u_{Lre}$ or $u_{Rre}$) is outputted from the position error compensating means 53 to approximation inverse kinematics calculation means 54. The current value $q_i$ ($q_L$ or $q_R$) of the joint angle vector, which is measured in the arm 3 (3a or 3b), is also inputted to the approximation inverse kinematics calculation means 54.

Moreover, when the joint lock mechanism 28 is locked, the position error compensating means 53, to which a joint lock instruction has been inputted from the joint lock mechanism control means 59, as will be described later, sets a servo gain for position error compensation to a low value, for example, ½ of the value in a non-locked state (sets the size of the position error compensating output $u_i$ to ½), so as to exert a function of lowering the servo rigidity for position control.

Supposing that an input to the approximation inverse kinematics calculation means 54 is $u_i$ and that an output from the approximation inverse kinematics calculation means 54 is $u_{iout}$, the approximation inverse kinematics calculation means 54 carries out approximation calculations of inverse kinematics based upon an approximation expression $u_{iout} = J_{ir}(q_i)^{-1} u_{iin}$. In this case, $J_{ir}(q_i)$ is a Jacob matrix that satisfies the relationship in the following equation:

$$\dot{r}_i = J_{ir}(q_i)\dot{q}_i \quad \text{[Formula 5]}$$

Based upon this formula, since an approximation expression $q_{ie} \approx J_{ir}(q_i)^{-1} r_{ie}$ is introduced, it is found that conversion from the tip-unit position-orientation error $r_{ie}$ ($r_{Le}$ or $r_{Re}$) to the joint angle error $q_{ie}$ ($q_{Le}$ or $q_{Re}$), that is, conversion from a value in the tip-unit coordinates relating to the error to a value in the joint coordinates, can be obtained by using the reverse Jacob matrix $J_{ir}(q_i)^{-1}$. In the same manner, with respect to the error compensating output, since conversion from the value in the tip-unit coordinates to a value in the joint coordinates is carried out based upon the reverse Jacob matrix $J_{ir}(q_i)^{-1}$, upon input of the position error compensation output $u_{ire}$ ($u_{Lre}$ or $u_{Rre}$) to the approximation inverse kinematics calculation means 54, a joint angle error compensating output $u_{iqe}$ ($u_{Lqe}$ or $u_{Rqe}$) for compensating for the joint angle error $q_{ie}$ ($q_{Le}$ or $q_{Re}$) is outputted from the approximation inverse kinematics calculation means 54. Symbol 52 represents forward kinematics calculation means to which a joint angle vector $q_i$ ($q_L$ or $q_R$) corresponding to the current value q of the joint angle measured by each of encoders 37 of the joint axes 12, 13, and 14, outputted from the arm 3 (3a or 3b), is inputted, and executes geometric calculations for conversion from the joint angle vector $q_i$ ($q_L$ or $q_R$) of the arm 3 (3a or 3b) to the tip-unit position vector $r_i$ ($r_L$, or $r_R$).

With respect to the impedance control means 45 (45a or 45b) thus structured as described above, the following description will discuss the principle of the operations thereof.

The basic operation is a feed-back controlling (position control) of the tip-unit position error $r_{ie}$ ($r_{Le}$ or $r_{Re}$) by the position error compensating means 53. By using, for example, a PID compensator as the position error compensating means 53, controlling operations are carried out so as to converge the tip-unit position error $r_{ie}$ ($r_{Le}$ or $r_{Re}$) to 0 so that a target operation of the arm 3 (3a or 3b) is realized.

In an impedance control mode, the tip-unit desired position compensating output $r_{id\Delta}$ ($r_{Ld\Delta}$ or $r_{Rd\Delta}$) is added to the tip-unit desired position value $r_{id}$ ($r_{Ld}$ or $r_{Rd}$) of the arm 3 (3a or 3b) by the impedance calculation means 46 (46a or 46b) so that the tip-unit desired position value $r_{id}$ ($r_{Ld}$ or $r_{Rd}$) is corrected. For this reason, the position control system has a target value of the tip unit position slightly deviated from the original value, with a result that the mechanical impedance is realized. Since the tip-unit desired position compensating output $r_{id\Delta}$ ($r_{Ld\Delta}$ or $r_{Rd\Delta}$) is calculated based upon equation (1), the mechanical impedance relating to inertia M, viscosity D, and rigidity K is realized.

By the principle of the impedance control means 45 (45a or 45b) described above, in a case where an operator of the robot holds with a hand the force detection external cover 36 that functions as one example of an external member of the arm 3 (3a or 3b), and applies a force to the force detection external cover 36, the arm 3 (3a or 3b) is operated in a direction of the applied force. Therefore, the arm 3 (3a or 3b) can be operated simply by holding and moving the arm 3 (3a or 3b) so that a positioning operation can be easily carried out.

The structure of waist mechanism impedance control means 45p is the same as that of the impedance control means 45 (45a or 45b), although the waist mechanism impedance control means 45 has one dimension. Calculations in waist impedance calculation means 50 are executed based upon the following equation (5) to obtain a waist angle target compensating output $q_{p\Delta d}$ by using the impedance parameters of inertia m, viscosity d, and elasticity k, as well as the current value $q_p$ of the waist angle and an external force $F_i$ ($F_L$ or $F_R$) detected by the force sensor 35, and the result is output. The waist angle target compensating output $q_{p\Delta d}$ is added to the waist angle degree target value $q_{pd}$ outputted from the target track generation means 48 so that a waist angle compensating target vector is generated.

[Formula 6]

$$q_{p\Delta d}=(s^2m+sd+l)^{-1}F_z \quad \text{Equation (5)}$$

In equation (5), s represents a Laplace operator, and $F_z$ is a value obtained by selecting a greater one in the absolute value between a vertical direction component $F_{Lz}$ of a detected value of the force sensor 35 of the left arm 3a and a vertical direction component $F_{Rz}$ of a detected value of the force sensor 35 of the right arm 3b. The selection of this value $F_z$ ($F_{Lz}$ or $F_{Rz}$) is carried out by force sensor selection means 51. Thus, even when an external force is inputted to either the force sensor 35 of the left arm 3a or the force sensor 35 of the right arm 3b, the waist mechanism 2 can be operated.

Figure 14:
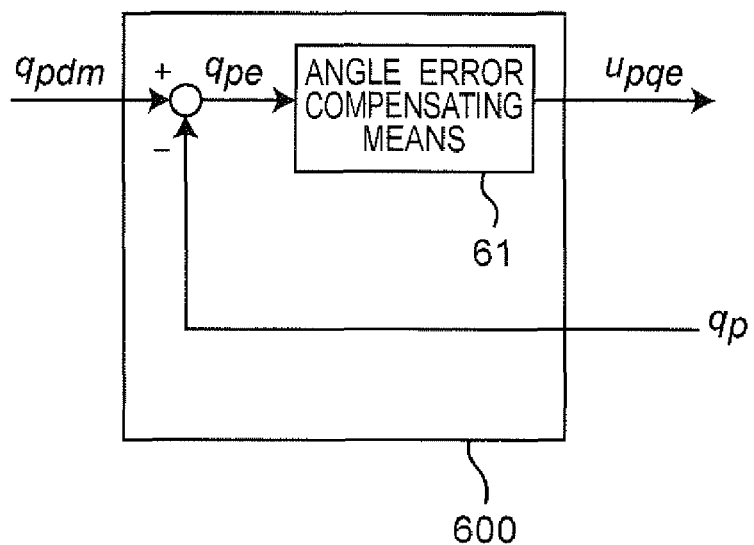
FIG. 14 is a view that shows a detailed structure of waist angle control means of the control apparatus of the robot according to the embodiment of the present invention.

Angle control means 60, which has a structure shown in FIG. 14, is designed so that a waist angle error $q_{pe}$ between the waist angle compensating target vector $q_{pdm}$ generated as described above and the waist angle $q_p$ is inputted to angle error compensating means 61, and a waist angle instruction value $u_{pqe}$ is outputted from the angle error compensating means 61 to the waist mechanism 2. By using, for example, a PID compensator as the angle error compensating means 61, controlling operations are carried out so as to converge the waist angle error $q_{pe}$ to 0 in the angle control means 60, thereby realizing a targeted operation of the waist mechanism 2.

In accordance with the waist mechanism impedance control means 45p thus structured as described above, when the operator of the robot holds and lifts up the force detection external cover 36 with a hand, of either the left arm 3a or the right arm 3b, or both thereof simultaneously, the waist mechanism 2 rises so that the entire arm 3 is raised. In contrast, when the operator holds and pulls down the force detection external cover 36 with a hand, the waist mechanism 2 is operated to fall forward so that the entire arm 3 is lowered.

The operation mode switching means 47, to which the tip-unit position vector $r_i$ ($r_L$ or $r_R$) is inputted from the position control means 49 (49a or 49b) and the current value $q_p$ of the waist angle is inputted from the waist mechanism 2, controls the operation sequence (which will be described later in detail) based upon an operation sequence chart shown in FIG. 15. Thus, switching of control modes among the left-arm impedance control means 45a, the right-arm impedance control means 45b, and the waist-mechanism impedance control means 45p, switching between a lock actuation and a lock release of the joint lock mechanism by using the joint lock mechanism control means 59, and operation instructions to the target track generation means are carried out. When the advance button 64 of the operation mode switcher 58 is pressed, the operation mode switching means 47 allows to proceed to a next sequence, and when the retreat button 65 of the mode switcher 58 is pressed, the operation mode switching means 47 allows to return to the previous sequence, so that control modes are switched in accordance with the respective steps in the respective sequences.

Moreover, in a case where the stop switch 66 of the operation mode switcher 58 is pressed, the operation mode switching means 47 stops the operation of the target track generation means 48, and switches the control mode of the left arm 3a and the right arm 3b to the position control mode, as well as switches the control mode of the waist mechanism 2 to the angle control mode, respectively. In a case where the operation of the target track generation means 48 is stopped, since the target track being outputted upon stopping is continuously outputted without being updated, the operations of the left arm 3a, the right arm 3b, and the waist mechanism 2 are respectively stopped, so that the operation of the robot is stopped. This stopping operation is effective in a case where the operation of the robot is desirably stopped immediately, for example, when an abnormal operation or the like occurs to the robot.

The operation mode switching means 47 carries out switching between the position control mode and the impedance control mode on each of the left arm impedance control means 45a, the right arm impedance control means 45b, and the waist mechanism impedance control means 45p. In the position control mode, the operation mode switching means 47 sets the output of the impedance calculation means 46 to 0 so that the operation of the arm 3 (3a or 3b) is allowed to function under a position control following the tip-unit desired position value, while in the impedance control mode, the operation mode switching means 47 makes the output of the impedance calculation means 46 (46a or 46b) effective so that the operation of the arm 3 (3a or 3b) functions under an impedance control so as to operate with a mechanical impedance characteristic having been set with respect to an external force.

In the same manner, with respect to the waist mechanism 2, the operation mode switching means 47 also sets the output of the waist impedance calculation means 50 to 0 in the angle control mode so as to function under a waist control, while in the impedance control mode, makes the output of the waist impedance calculation means 50 effective so that the waist mechanism 2 functions under an impedance control so as to operate with a mechanical impedance characteristic having been set with respect to an external force.

Moreover, the operation mode switching means 47 sends an instruction to the joint lock mechanism control means 59 so that controlling operations of a lock actuation and a lock release are carried out on the joint lock mechanism 28.

Information as to whether or not the arm 3 (3a or 3b) is lifting a load such as a heavy object is inputted to the joint lock mechanism control means 59 from the operation mode switching means 47, and only in a case where the operation mode switching means 47 determines that no load such as a heavy object is being lifted, the joint lock mechanism control means 59 carries out the lock releasing operation on the joint lock mechanism 28. While, upon determination by the operation mode switching means 47 that a load such as a heavy object is being lifted, the joint lock mechanism control means 59 carries out an interlocking operation so that no lock releasing operation is carried out on the joint lock mechanism 28. Accordingly, since it is possible to prevent the lock of the joint lock mechanism from being erroneously released by the joint lock mechanism control means 59 when the arm 3 (3a or 3b) is lifting a load such as a heavy object, the safety can be further improved.

Moreover, the joint lock mechanism control means 59 sends a joint-locking instruction to the position error compensating means 53 so as to lower the servo rigidity of the position control when the joint is locked. Thus, it is possible to prevent a rotation movement of the joint from being unnecessarily generated by the position control by the position error compensating mean 53, and also to prevent the fixed opposing gear 29 and the movable opposing gear 30 from being mutually meshed by an unnecessarily high force, therefore, upon releasing the joint lock mechanism, it is possible to reduce friction between the teeth surfaces of the fixed opposing gear 29 and the movable opposing gear 30 being in contact with each other upon releasing the joint lock mechanism, and consequently to carry out the releasing operation smoothly.

The target track generation means 48 outputs a tip-unit desired position vector $r_{id}$ ($r_{Ld}$ or $r_{Rd}$) used for achieving a targeted operation of the arm 3 (3a or 3b). The targeted operation of the arm 3 (3a or 3b) is preliminarily inputted to the target track generation means 48 as pieces of information ($r_{id0}, r_{id1}, r_{id2}, \ldots$) that is, ($r_{Ld0}, r_{Ld1}, r_{Ld2}, \ldots$) or ($r_{Rd0}, r_{Rd1}, r_{Rd2}, \ldots$) for each of passage points in accordance with a targeted job, as numeric values with use of a keyboard as one example of external input means (external input device) 93 of the control apparatus 38, and the target track generation means 48 interpolates the track between the respective points by using polynomial interpolation so that a tip-unit desired position vector $r_{id}$($r_{Ld}$ or $r_{Rd}$) is generated. With respect to the waist angle degree target value (waist angle degree target vector) $q_{pd}$, in the same manner as in the operation of the arm 3 (3a or 3b), a targeted track of the angle control operation of the waist mechanism 2 (in other words, rocking operations of the body unit 8) is also generated by the target track generation means 48. That is, pieces of positional information ($q_{pd0}, q_{pd1}, q_{pd2}, \ldots$) for each of passage points are preliminarily inputted to the target track generation means 48 by the external input means 93 as numeric values in accordance with a targeted job, and the target track generation means 48 interpolates the track between the respective points by using polynomial interpolation so that a waist angle target vector $q_{pd}$ is generated.

In the position control mode of the arm 3 (3a or 3b) or in the angle control mode of the waist mechanism 2, the operation mode switching means 47 specifies the pieces of positional information for passage points ($r_{id0}, r_{id1}, r_{id2}, \ldots$) that is, $r_{Ld0}$, $r_{Ld1}, r_{Ld2}, \ldots$) or ($r_{Rd0}, r_{Rd1}, r_{Rd2}, \ldots$) or ($q_{pd0}, q_{pd1}$, $q_{pd2}, \ldots$), and causes the target track generation means 48 to carry out track interpolating operation.

Moreover, in the impedance control mode, it stops the track interpolating operation by the target track generation means 48, and causes the target track generation means 48 to maintain the tip-unit desired position value $r_{id}$ ($r_{Ld}$ or $r_{Rd}$) or the waist angle target value $q_{pd}$ obtained instantaneously upon switching into the impedance control mode. Furthermore, when switching is made from the impedance control mode to the position control mode, or from the impedance control mode to the angle control mode, it causes the target track generation means 48 to set the tip-unit position $r_i$ ($r_L$ or $r_R$) or the waist angle $q_p$ obtained instantaneously upon switching as a start point of the target track, and also causes the target track generation means 48 to newly carry out track interpolating operations from the start point.

Figure 16:
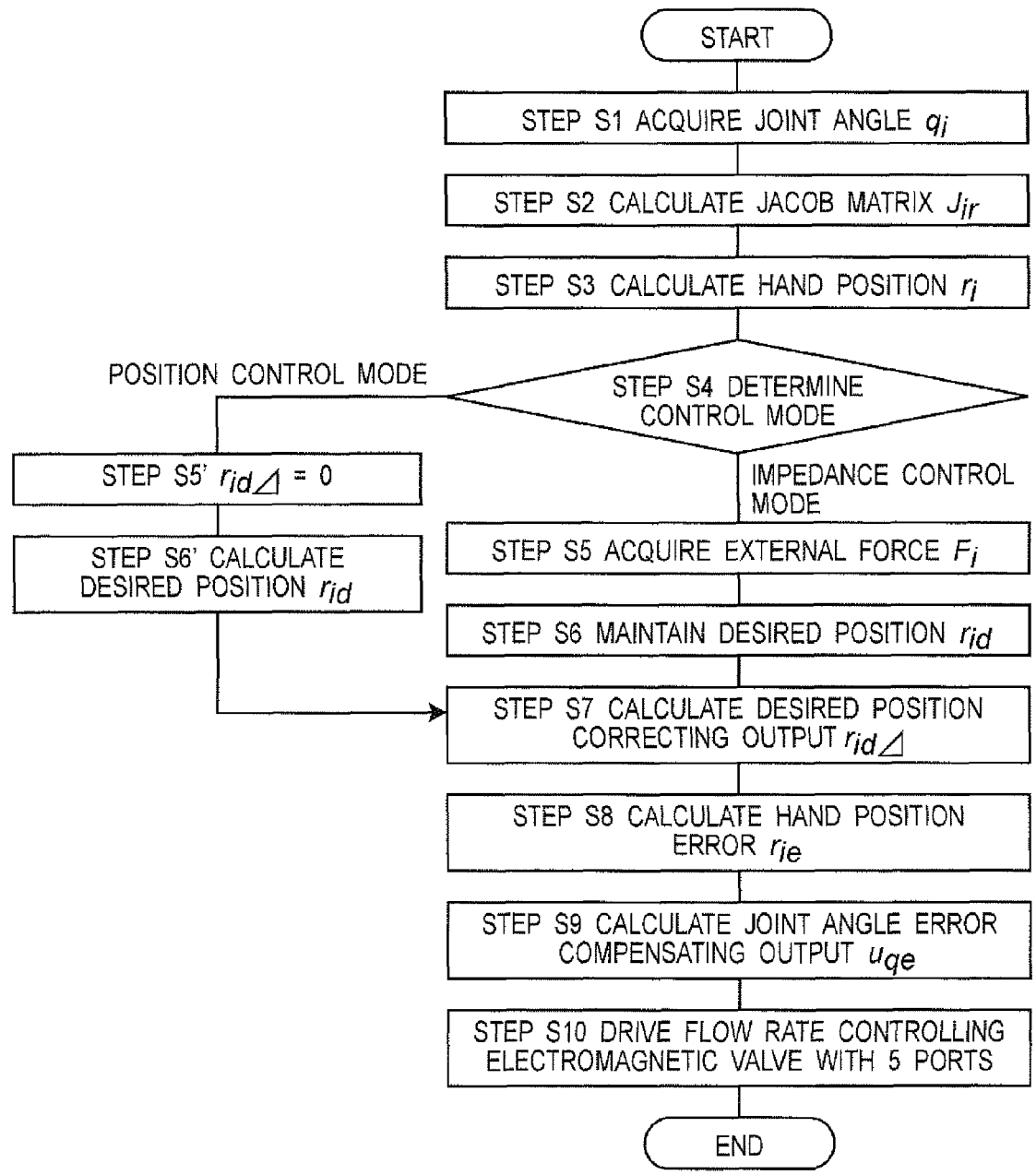
FIG. 16 is a flow chart that shows operation steps of the control program in impedance control means of the control apparatus of the robot according to the embodiment of the present invention.

Referring to a flow chart of FIG. 16, the following description will discuss actual operation steps of the control program 39 based upon the principle described above.

First, in step S1, joint angle data (joint variable vector or joint angle vector $q_i$) ($q_L$, or $q_R$), measured by each of the encoders 37, is received by the control apparatus 38.

Next, in step S2, calculations such as a Jacob matrix $J_{ir}$($J_{Lr}$ or $J_{Rr}$), required for kinematics calculations for the arm 3 (3a or 3b), are carried out by the approximation inverse kinematics calculation means 54.

Next, in step S3, the current tip-unit position vector $r_i$($r_L$ or $r_R$) of the arm 3 (3a or 3b) is calculated by the forward kinematics calculation means 52 based upon the joint angle data (joint angle vector $q_i$) ($q_L$ or $q_R$) from the arm 3 (3a or 3b), and the current tip-unit position vector $r_i$($r_L$ or $r_R$) thus calculated is outputted (process in the forward kinematics calculation means 52).

Next, in step S4, the instruction of control mode from the operation mode switching means 47 is determined by the target track generation means 48 (in other words, based upon the instruction value from the operation mode switching means 47, the target track generation means 48 determines whether the control mode is in the position control mode or the impedance control mode), and upon determination by the target track generation means 48 that the control mode is in the impedance control mode, the process proceeds to step S5, while upon determination by the target track generation means 48 that the control mode is in the position control mode, the process proceeds to step S5', respectively.

In step S5, in the case of the impedance control mode, an external force $F_i$($F_L$ or $F_R$), measured by the force sensor 35, is received by the impedance calculation means 46 (46a or 46b) of the control apparatus 38.

In succession to step S5, in step S6, in the case of the impedance control mode, the tip-unit position vector $r_i$ ($r_L$ or $r_R$) (the tip-unit position vector $r_i$ ($r_L$ or $r_R$) calculated in the forward kinematics calculation means 52 and inputted to the target track calculation means 48 through the operation mode switching means 47 as shown in FIG. 12), obtained instantaneously upon switching to the impedance control mode, is recorded by the target track calculation means 48, and is outputted as the tip-unit desired position vector $r_{id}$ ($r_{Ld}$ or $r_{Rd}$) and then held by the impedance control means 45 (45a or 45b).

In succession to step 56, in step S7, in the case of the impedance control mode, based upon the mechanical impedance parameters, namely, inertia M, viscosity D, and elasticity K that are preliminarily set in the impedance calculation means 46 (46a or 46b), as well as based upon an external force $F_i$ ($F_L$ or $F_R$) that is measured by the force sensor 35 and is applied to the arm 3 (3a or 3b), a tip-desired position compensating output $r_{id\Delta}$ ($r_{Ld\Delta}$ or $r_{id\Delta}$) is calculated by the impedance calculation means 46 (process in the impedance calculation means 46). Thereafter, the process proceeds to step S8.

On the other hand, in step S5', in the case of the position control mode, the tip-desired position compensating output $r_{id\Delta}$ ($r_{Ld\Delta}$ or $r_{Rd\Delta}$) is set to 0 vector by the impedance calculation means 46 (process in the impedance calculation means 46).

In succession to step S5', in step S6', a tip-unit desired position vector $r_{id}$ ($r_{Ld}$ or $r_{Rd}$) of the arm 3 (3a or 3b) is calculated by the target track calculation means 48 so that the calculated tip-unit desired position vector $r_{id}$ ($r_{Ld}$ or $r_{Rd}$) is outputted to the impedance control means 45 (45a or 45b). Thereafter, the process proceeds to step S8.

In step S8, the sum of the tip-unit desired position vector $r_{id}$ ($r_{Ld}$ or $r_{Rd}$) and the tip-unit desired position compensating output $r_{id\Delta}$ ($r_{Ld\Delta}$ or $r_{\Delta}$) is calculated by the impedance control means 45 (45a or 45b), and an error $r_{ie}$ ($r_{Le}$ or $r_{Re}$) of the tip-unit position, which corresponds to a difference between the tip-unit position compensation target vector $r_{idm}$ ($r_{Ldm}$ or $r_{Rdm}$) as the result of the calculation and the current tip-unit position vector $r_i$ ($R_L$ or $r_R$) calculated by the forward kinematics calculation means 52 and outputted therefrom, is calculated by the position error compensating means 53 (process in the position error compensating means 53). A PID compensator may be proposed as a specific example of the position error compensating means 53. By appropriately adjusting three gains, namely, a proportional gain, a differential gain, and an integral gain, corresponding to an orthogonal matrix of a constant, the control operation of the position error compensating means 53 is carried out so as to converge the position error to 0.

Next, in step S9, the position error compensation output $u_{ire}$ ($u_{Lre}$ or $u_{Rre}$) is multiplied by the reverse matrix of Jacob matrix $J_{ir}$($J_{Lr}$ or $J_{Rr}$) calculated in step S2, in the approximation inverse kinematics calculation means 54, so that the position error compensation output $u_{ire}$ ($u_{Lre}$ or $u_{Rre}$) is converted from a value relating to an error of the tip-unit position to a joint angle error compensating output $u_{iqe}$ ($u_{Lqe}$ or $u_{Rqe}$) that is a value relating to an error of the joint angle by the approximation inverse kinematics calculation means 54 (process in the approximation inverse kinematics calculation means 54).

Next, in step S10, the joint angle error compensating output $u_{iqe}$ ($u_{Lqe}$ or $u_{Rqe}$) is provided from the approximation inverse kinematics calculation means 54 to the flow-rate controlling electromagnetic valve 27 with 5 ports through the D/A board 41 so that, by changing a voltage to be applied to the electromagnet of the flow-rate controlling electromagnetic valve 27 with 5 ports, the pneumatic artificial muscles 15a, 15b, 15c, 15d, 16a, 16b, 17a, 17b, 17c, and 17d are respectively driven. Thus, rotating movements of the respective joint axes 12, 13 and 14 of the arm 3 (3a or 3b) and rocking movements of the waist mechanism 2 are respectively generated.

By repeatedly executing the above-mentioned steps S1 to S10 as controlling calculation loops, control of the operations of the arm 3 (3a or 3b) and the waist mechanism 2 is achieved.

Next, the following description will discuss a flow of an operation sequence and switching of control modes of the transporting job, with reference to the sequence chart of FIG. 15 and operation views of FIGS. 17A to 17D.

<Sequence 1 (Home Position)>

Figure 17A:
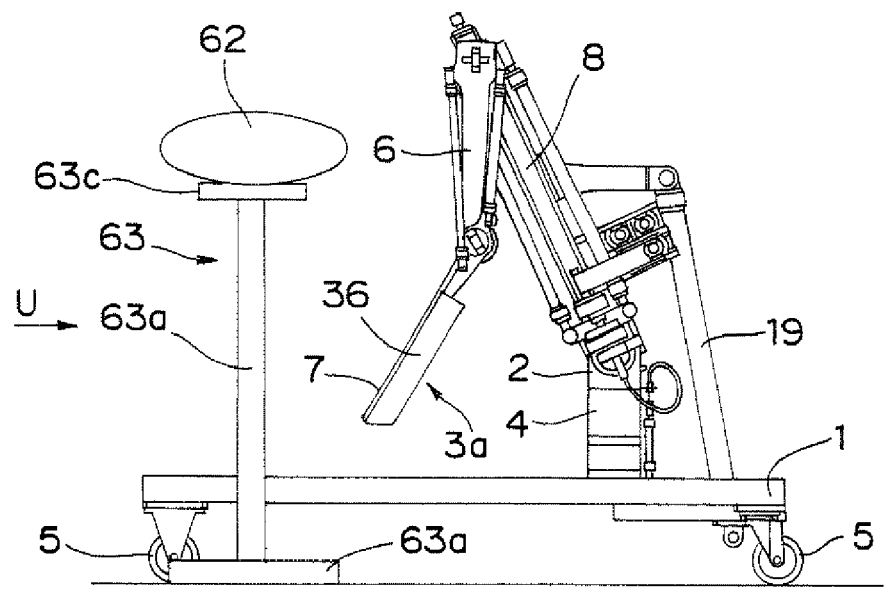
FIG. 17A is an operation view for explaining transporting operations of the robot according to the embodiment of the present invention.

In sequence 1 (home position), the left arm 3a and the right arm 3b are set into the position control mode, and the waist mechanism 2 is set into the angle control mode so that the left arm 3a, the right arm 3b, and the waist mechanism 2 are respectively operated to bring the robot to a basic orientation shown in FIG. 17A.

<Sequence 2 (Left Arm Operation)>

Figure 17B:
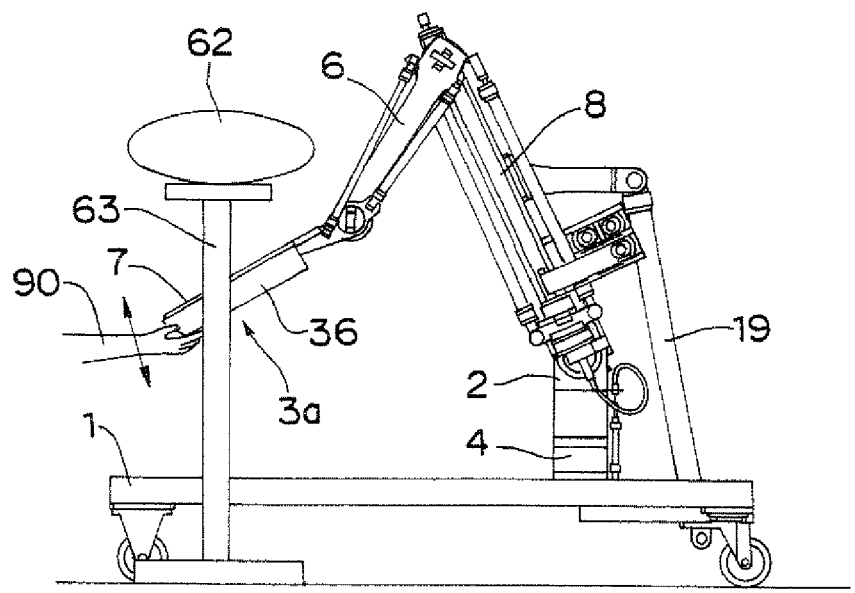
FIG. 17B is an operation view for explaining other transporting operations of the robot according to the embodiment of the present invention.

In sequence 2 (left arm operation), the left arm 3a is set into the impedance control mode, and in a case where an operator applies a force with a hand 90 to the force detection external cover 36 of the second link 7 of the left arm 3a, since the left arm 3a is made operable, the person (operator) is allowed to operate the left arm 3a by grabbing the force detection external cover 36 of the second link 7 of the left arm 3a with the hand 90 so that, through a state as shown in FIG. 17B, the left arm 3a is inserted and placed below a transporting object 62, to be brought into a transporting object support preparation state shown in FIG. 17O.

By allowing a supporting leg 63 for supporting the transporting object 62 to have, for example, a structure as shown in FIG. 18, which is a view seen in a direction indicated by an arrow U in FIG. 17A, it becomes possible to easily insert the arm below the transporting object 62 to be disposed therebelow. That is, in FIG. 18, the supporting leg 63 has a structure in which two lateral struts 63b are bridged between a pair of longitudinal struts 63a each having a lower end secured onto a supporting plate 63d and an upper end to which a transporting object mounting plate 63c is secured, and in a state where a transporting object 62 is mounted on the paired transporting object mounting plates 63c, a space 63p that allows the left arm 3a and the right arm 3b to be inserted therein is provided between the paired longitudinal struts 63a. Therefore, the force detection external cover 36 of the second link 7 of the left arm 3a, grabbed by the hand 90 of the person (operator), is inserted into this space 63p to be disposed therein so that the second link 7 of the left arm 3a can be placed below one of the sides of the transporting object 62.

Moreover, upon carrying out a lift-up job in nursing care, a care giver lifts the upper body or the legs of a person to be cared so as to be raised slightly from the bed or the like, so that the left arm 3a is inserted into the resulting gap.

<Sequence 3 (Right Arm Operation)>

In sequence 3 (right arm operation), the right arm 3b is set into the impedance control mode. When the operator applies a force with the 90 to the force detection external cover 36 of the second link 7 of the right arm 3b, since the right arm 3b is made operable, the person (operator) is allowed to operate the right arm 3b by grabbing the force detection external cover 36 of the second link 7 of the right arm 3b with the hand 90, and the right arm 3b is inserted and placed below the transporting object 62 (the right arm 3b is placed at a position similar to the position of the left arm 3a of FIG. 17C so as to be brought into a transporting object support preparation state). In this case, the left arm 3a is switched into the position control mode to be held at the position (position of FIG. 17C) related to the operation of sequence 2, with the orientation being secured (the operation of the right arm 3b is carried out in the same manner as in the operation of the left arm 3a of FIG. 17B and FIG. 17C).

<Sequence 4 (Joint Lock)>

In sequence 4 (joint lock), the respective joint lock mechanisms 28 of all the joints 9, 10, and 11 of the left arm 3a and the right arm 3b are operated so that all the joints 9, 10, and 11 are secured, and orientations of the left arm 3a and the right arm 3b are subsequently secured. In this case, the right arm 3b is switched into the position control mode, and is held at the position (position of FIG. 17O) related to the operation of sequence 3, and the orientation is secured as it is. Since the left arm 3a is kept in the switched state into the position control mode, both of the left arm 3a and the right arm 3b are brought into the switched state into the position control mode so that the orientations of the left arm 3a and the right arm 3b are respectively secured.

<Sequence 5 (Lift)>

In sequence 5 (lift), the waist mechanism 2 is switched into the impedance control mode, and when the person (operator) applies a force to the force detection external cover 36 of the second link 7 of either one of the arms 3 of the left arm 3a or the right arm 3b with the hand 90, the waist mechanism 2 is made operable. Therefore, when the person (operator) grabs with the hand 90 the force detection external cover 36 of the second link 7 to push up the second link 7, both of the left arm 3a and the right arm 3b are raised simultaneously by the operation of the waist mechanism 2 so that the transporting object 62 can be lifted. Thus, the process proceeds from the transporting object supporting preparation state of FIG. 17C to a transporting object lifting state shown in FIG. 17D. In this case, when the person (operator) grabs the force detection external cover 36 of the second link 7 to pull down the second link 7, the left arm 3a and the right arm 3b are lowered by the operation of the waist mechanism 2, so that the transporting object 62 can be lowered. Thus, the process returns to the state of FIG. 17C in which the transporting object 62 is supported by the supporting leg 63.

<Sequence 6 (Joint Lock Release)>

Figure 17C:
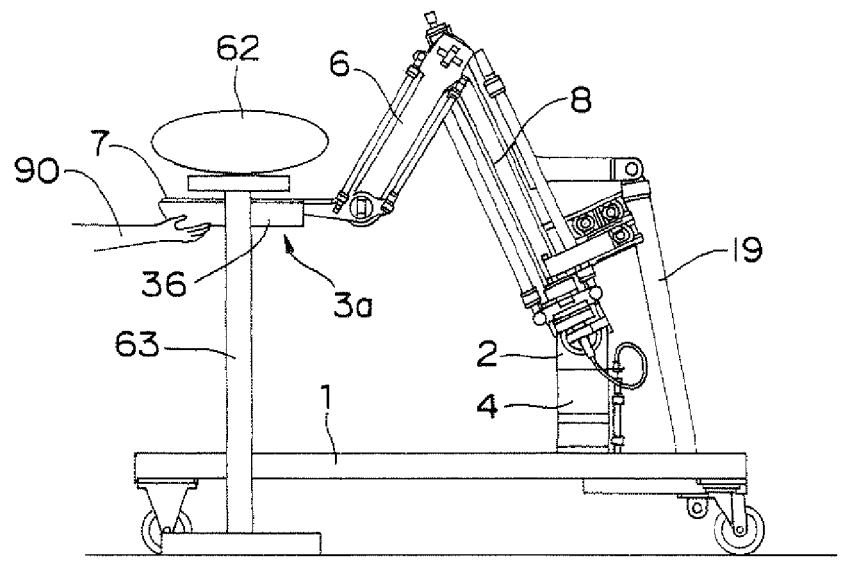
FIG. 17C is an operation view for explaining other transporting operations of the robot according to the embodiment of the present invention.
Figure 17D:
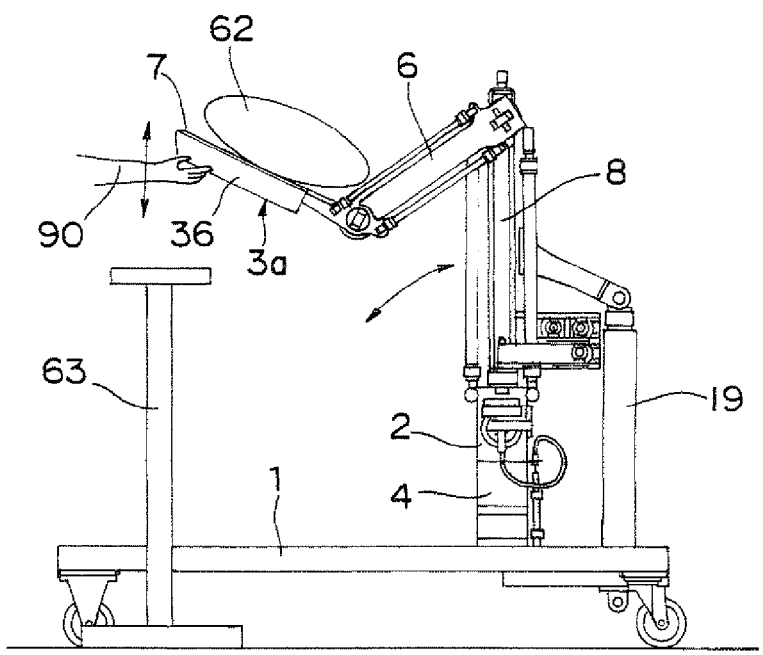
FIG. 17D is an operation view for explaining other transporting operations of the robot according to the embodiment of the present invention.

In sequence 6 (joint lock release), in the state of FIG. 17C where the transporting object 62 is supported by the supporting leg 63, the respective joint lock mechanisms 28 of all the joints 9, 10, and 11 of the left arm 3a and the right arm 3b are operated so that the fixed states of all the joints 9, 10, and 11 are released. The control of each of the left arm 3a and the right arm 3b is kept in the position control mode so that the respective positions of the left arm 3a and the right arm 3b are maintained.

<Sequence 7 (Left Arm Operation)>

In sequence 7 (left arm operation), in the state of FIG. 17C where the transporting object 62 is supported by the supporting leg 63, the left arm 3a is set into the impedance control mode. Since the left arm 3a is made operable when a force is applied to the force detection external cover 36 of the second link 7 of the left arm 3a with the hand 90, the person (operator) is allowed to operate the left arm 3a by grabbing the force detection external cover 36 of the second link 7 with the hand 90, so that the left arm 3a is removed from the space 63p below the transporting object 62 supported by the supporting leg 63, and the process returns to the initial state shown in FIG. 17A through the state shown in FIG. 17B.

<Sequence 8 (Right Arm Operation)>

In sequence 8 (right arm operation), in the state of FIG. 17C where the transporting object 62 is supported by the supporting leg 63, the right arm 3b is set into the impedance control mode. Since the right arm 3b is made operable when a force is applied to the force detection external cover 36 of the second link 7 of the right arm 3b with the hand 90, the person (operator) is allowed to operate the right arm 3b by grabbing the force detection external cover 36 of the second link 7 with the hand 90, so that the right arm 3b is removed from the space 63p below the transporting object 62 supported by the supporting leg 63. Thereafter, the process returns to sequence 1, and by repeating these steps (sequences), it is possible to carry out continuous operations.

With respect to the above-mentioned operation sequences, the operation mode switching means 47 makes the process proceed to the next sequence each time the advance button 64 of the operation mode switcher 58 is pressed, and also makes the process return to a previous sequence each time the retreat button 65 thereof is pressed, so that a series of operations can be realized and a transporting job or a lift-up job in nursing care can be achieved.

In accordance with the embodiments of the present invention, since the robot is provided with the joint lock mechanism 28, the arms 3a and 3b can hold a heavy load of the transporting object 62 by the mechanism thereof when the joints 9, 10, and 11 are locked. Therefore, it is not necessary to provide a strong actuator and the arms 3 can be light weighted. Moreover, when the joints 9, 10, and 11 are made free, a large degree of freedom due to the arm structure can be effectively utilized so that the degree of freedom in positioning the transporting object 62 can be increased, thereby providing a robot easily used.

Moreover, since the waist mechanism 2 is included in addition to the arm 3 provided with the joint lock mechanism 28, a strong actuator for use in lifting a heavy object is only required to the waist mechanism 2, thereby achieving a simple and light weighted structure with high power.

Moreover, since the joint lock mechanism 28 is provided as a one-way clutch mechanism, even a heavy load of the transporting object 62 can be received by the mechanism, and even after positioning the arm 3 with the joints being locked, a re-adjusting operation can be carried on a movable direction of the one-way clutch mechanism. That is, in the state where the joint lock mechanism 28 is locked, the robot operation control means 44 carries out in the robot arm operation mode on one of the joints in response to an external force exerted in the movable direction of the one-way clutch mechanism, while in response to an external force exerted in a non-movable direction of the one-way clutch mechanism, the robot arm operation mode is prevented. Moreover, in a case where, upon carrying out a lifting or lowering operation by the waist mechanism 2 after the joints have been locked, the arm 3 is brought into contact with an object or the like located below the arm 3, the one-way clutch mechanism is possible to weaken an impact force of the arm 3 applied to the object or the like, and consequently to ensure safety.

Moreover, by including the control apparatus 38 that controls operations while carrying out switching between the impedance control mode and the position control mode, as well as carrying out switching of the joint lock mechanism 28, it becomes possible to continuously carry out operations such as the positioning of the arm 3 and the lifting or the like of the transporting object 62, and by including the force sensor 35 and carrying out the impedance control, it becomes possible to realize an operation method that is easily understood in an intuitive manner, that is, an operation method that allows the operator to directly operate the arm 3 with the hand 90, and consequently to provide a robot further easily used.

Figure 19:
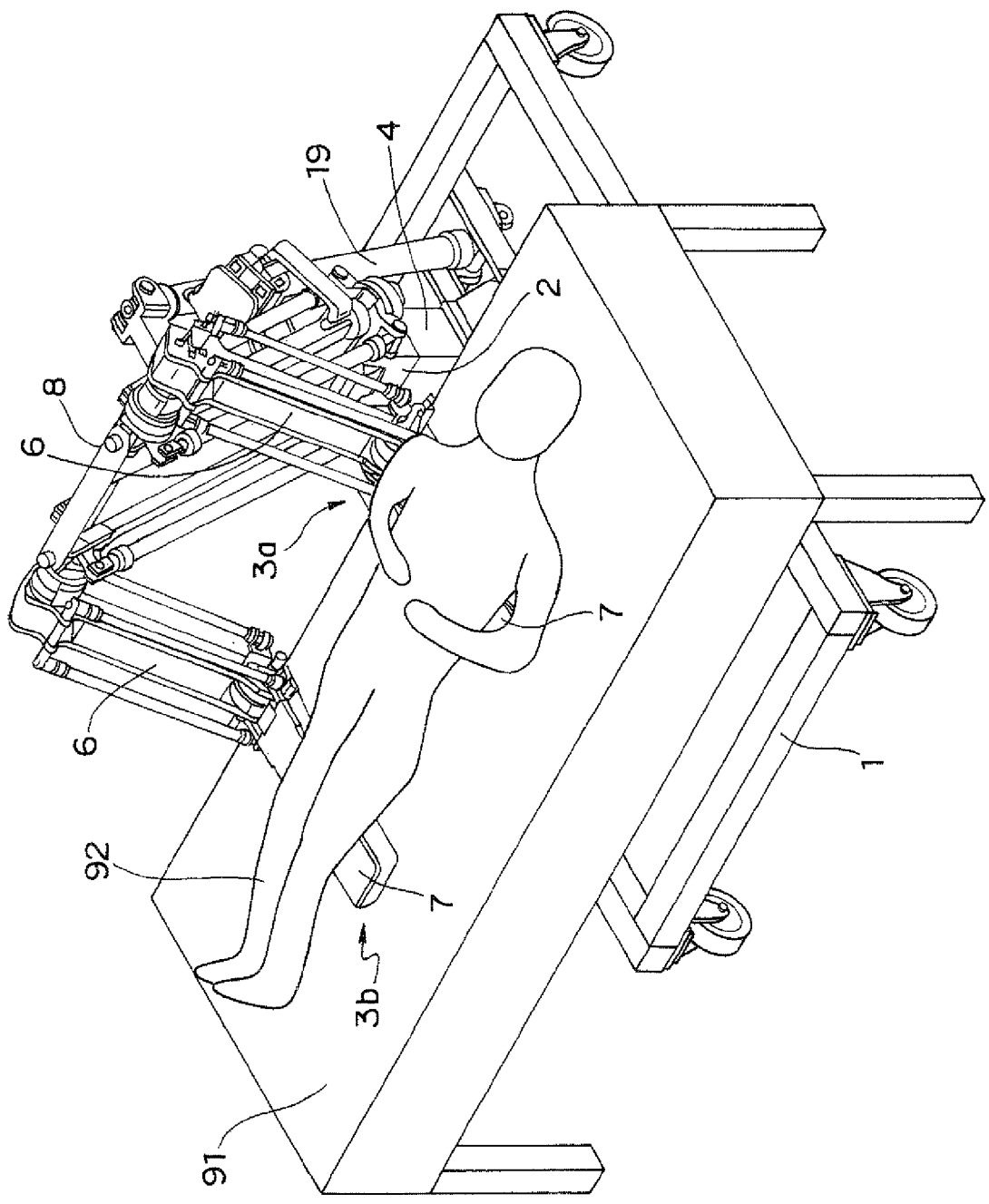
FIG. 19 is an explanatory view that shows a state in which the arm of the robot according to the embodiment of the present invention is applied to nursing care.

The robot in accordance with the embodiment described above of the present invention can be applied to nursing care where, as shown in FIG. 19, a person 92 to be cared who is lying on a bed 91 is held up and transported. Upon carrying out the lift-up job in nursing care, a care giver slightly lifts the upper body of the cared person 92 who is lying on the bed 91, and, for example, the care giver (operator) grabs the left arm 3a with the hand 90 to operate the left arm 3a so that the left arm 3a is inserted below the upper body of the person 92 to be cared. Thereafter, the care giver slightly raises the leg portions of the person 92 to be cared, and the care giver (operator) grabs the right arm 3b with the hand 90 to operate the right arm 3b so that the right arm 3b is inserted below the leg portions of the person 92 to be cared. Thereafter, the lifting operation of the person 92 to be cared can be carried out by the waist mechanism 2, after the respective joints 9, 10, and 11 of the left arm 3a and the right arm 3b have been locked by the respective joint lock mechanisms 28.

In the present embodiment, the driving of the arm 3 is carried out with use of a pneumatic artificial muscle. However, not limited to this, the driving may be carried out with use of a motor. In the case of driving the arm 3 with a motor also, by providing the joint lock mechanism 28, in view of the fact that the motor is not subjected to a load applied by a transporting object, it becomes possible to use a small and light weighted motor and consequently to provide a light weighted robot.

Figure 20:
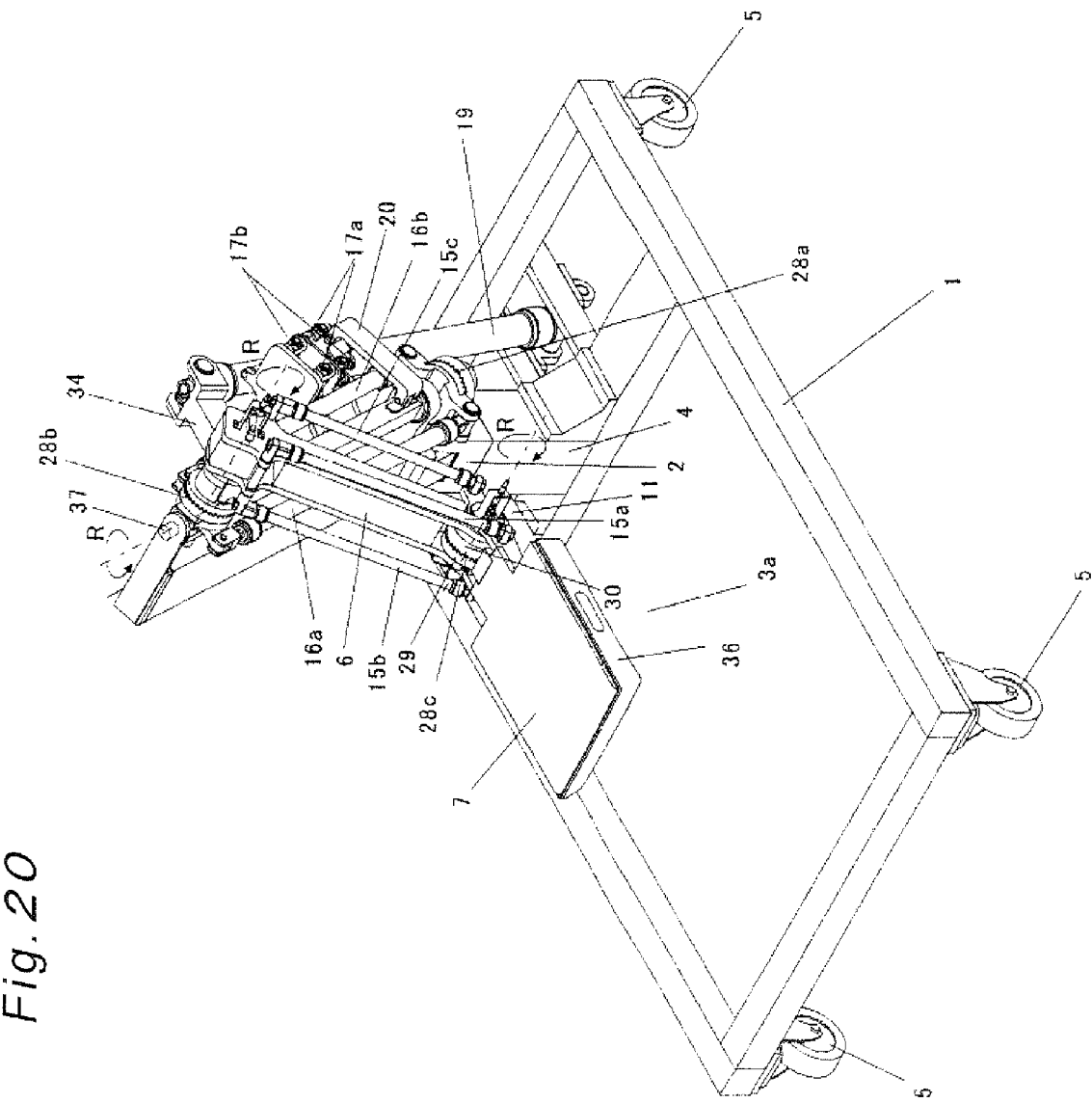
FIG. 20 is a perspective view that shows a mechanical structure in which the robot according to the embodiment of the present invention has a single arm.

Moreover, in the present embodiment, the structure having the two arms 3a and 3b is used. However, not limited to this structure, as shown in FIG. 20, a different structure having a single arm 3a may be applicable, and in which case also, a lifting operation for a transporting object can be carried out in the same manner. Since the number of arms is made smaller, it is possible to reduce the number of parts, and consequently to provide a further light weighted robot arm.

Figure 21:
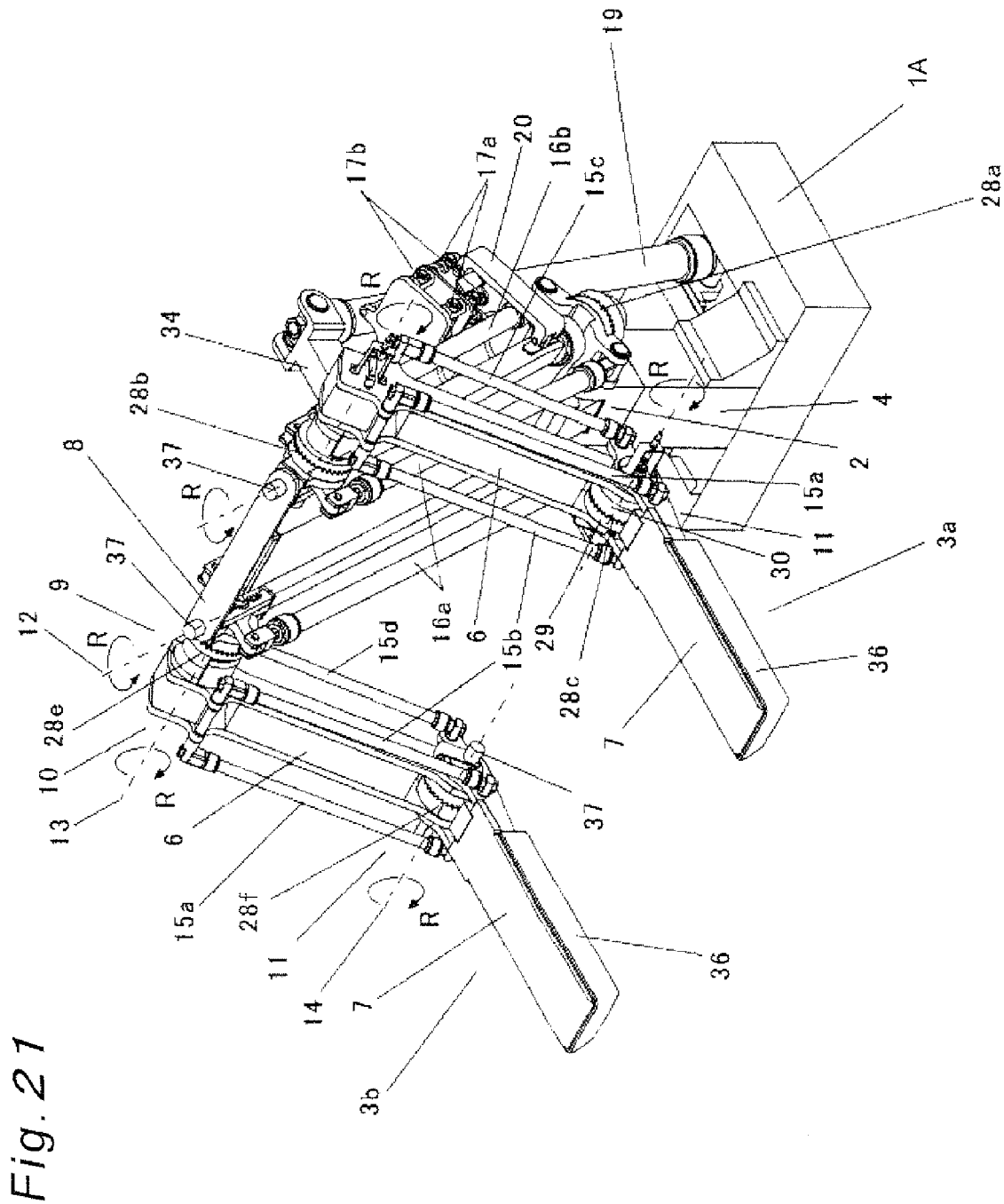
FIG. 21 is a perspective view that shows a mechanical structure in which the robot according to the embodiment of the present invention has a fixed arm.

Furthermore, in the present embodiment, a movable mode with use of the wheels 5 is adopted. However, not limited to this, a fixed-type robot, as shown in FIG. 21, with the strut 4 being secured to a fixed base 1A, may be applied to obtain similar operations.

In the present embodiment, the operation sequences are carried out as shown in the operation sequence chart shown in FIG. 15, with the left arm 3a and the right arm 3b being operated respectively. However, not limited to this, a different structure may be used in which, by operating either one of the arms, the other arm is allowed to synchronously carry out the same operation or a laterally symmetrical operation. In this case, the operation mode switching means 47 sets the arm to be operated into the impedance control mode, with the synchronizing arm being set into the position control mode, so that, upon carrying out the same operation, the target value of the tip-unit position of the synchronizing arm is set to a tip-unit position $r_i$ ($r_L$ or $r_R$) of the arm to be operated, while, upon carrying out the laterally symmetrical operation, the target value of the tip-unit position of the synchronizing arm is set to a minus value obtained by inverting only the horizontal direction component of the tip-unit position $r_i$ ($r_L$, or $r_R$) of the arm to be operated.

Furthermore, by using not a structure in which the left arm 3a and the right arm 3b are simultaneously moved synchronously as described above, but a structure in which, upon operating one of the arms, the track or the final arrival point of the tip-unit position $r_i$ ($r_L$, or $r_R$) of the arm is recorded, the other arm is then operated in the position control mode in the next sequence along the recorded track up to the final arrival point so as to be synchronized with each other with a time difference.

Moreover, in the present embodiment, with respect to the impedance control mode for operating the waist mechanism 2, the explanation has been given, with the impedance parameters, namely, inertia m, viscosity d, and elasticity k, as constant values. However, not limited to this, these parameters may be set to be changed in the operation mode switching means 47. For example, the viscosity d is first set to a great value, such as 20, and when the force sensor 35 detects a force and a lifting operation is started by the waist mechanism 2, this value is gradually reduced to a smaller value, for example, such as 5, in two seconds or the like. In this case, upon starting the lifting operation, the viscosity is strong to exert a function of preventing the waist mechanism 2 from moving abruptly. When the lifting operation is continuously carried out, the viscosity is gradually weakened so that the operation can be carried out with a lighter force. By making the impedance parameters variable in this manner, it is possible to realize a safe and smooth job even upon carrying out a lifting operation for a heavy object.

Moreover, by properly combining the arbitrary embodiments of the aforementioned various embodiments, the effects possessed by the embodiments can be produced.

Industrial Applicability

The robot, the control unit, the control method, and the control program of the robot of the present invention can be effectively applicable to a robot that carries out nursing care such as a lift-up job or the like in home or welfare facilities or the like, as well as to a robot that carries out a lift-up or transporting operation of an article, such as a heavy object. Moreover, not limited to such a house-service robot, the present invention is also applicable to an industrial robot or a movable mechanism for transporting a heavy object in a production facility or the like.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The invention claimed is:

1. A robot comprising:
   a base unit;
   a body unit;
   a body unit shifting mechanism that connects the base unit to the body unit so as to relatively shift the body unit relative to the base unit;
   a robot arm that is disposed on the body unit, and has a plurality of links and joint lock mechanisms capable of respectively mechanically securing a joint coupling the plurality of links to one another and a joint coupling one of the plurality of links and the body unit;
   an actuator for the robot arm, that drives the joint of the robot arm so as to drive to pivot the plurality of links;
   an actuator for a waist joint, that drives the body unit through the body unit shifting mechanism so as to relatively shift relative to the base unit;
   actuators for the joint lock mechanisms, that drive the joint lock mechanisms;
   an external force detection device that is installed in the robot arm and detects an external force applied to the robot arm by an operator; and
   a robot operation control unit that, based upon the external force detected by the external force detection device, carries out control operations of impedance control of one of the robot arm and the body unit shifting mechanism and position control of the other one of the robot arm and the body unit shifting mechanism while successively switching between the robot arm and the body unit shifting mechanism, and upon carrying out the impedance control on the body unit shifting mechanism, brings the joint lock mechanism of the robot arm into a secured state.

2. The robot according to claim 1, wherein the robot operation control unit controls while successively switching among a sequence in which the robot arm is impedance-controlled and the body unit shifting mechanism is position-controlled so as to operate the robot arm and position the robot arm relative to a job object, a sequence in which the robot arm is position-controlled and the body unit shifting mechanism is impedance-controlled so as to operate the body unit shifting mechanism to lift up the job object, and a sequence in which the robot arm is impedance-controlled and the body unit shifting mechanism is position-controlled so as to operate the robot arm and separate the robot arm from the job object.

3. The robot according to claim 1, wherein the robot operation control unit carries out an interlocking so as not to release the secured state of the joint lock mechanism in a state where the job object is being lifted.

4. The robot according to claim 1, wherein the body unit shifting mechanism is a waist mechanism that rocks the body unit substantially forward and rearward around the waist joint relative to the base unit.

5. The robot according to claim 4, wherein the waist mechanism has one end secured to the base unit and another end secured to the body unit so as to be driven by a translation driving actuator that drives the waist joint and rock the body unit substantially forward and rearward around the waist joint relative to the base unit.

6. The robot according to claim 1, wherein the joint lock mechanism is a one-way clutch mechanism.

7. The robot according to claim 6, wherein, when the joint lock mechanism is in a locked state, the robot operation control unit carries out the robot arm operation mode on one of the joints in response to an external force exerted in a movable direction of the one-way clutch mechanism, and does not carry out the robot arm operation mode in response to an external force exerted in a non-movable direction of the one-way clutch mechanism.

8. The robot according to claim 6, wherein, when the joint lock mechanism is in a locked state, the robot operation control unit carries out position control on the robot arm by using a servo rigidity lower than a servo rigidity in a non-locked state.

9. A robot control apparatus for controlling an operation of a robot comprising:
a base unit; a body unit; a body unit shifting mechanism that connects the base unit to the body unit so as to relatively shift the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the joint of the robot arm so as to drive to pivot the plurality of links; an actuator for a waist joint, that drives the body unit through the body unit shifting mechanism so as to relatively shift relative to the base unit; and actuators for the joint lock mechanisms, that drives the joint lock mechanisms,
based upon an external force detected by an external force detection device that is disposed on the robot arm and detects an external force applied to the robot arm by an operator, the control apparatus carrying out control operations of impedance control of one of the robot arm and the body unit shifting mechanism and position changed to control of the other one of the robot arm and the body unit shifting mechanism while successively switching between the robot arm and the body unit shifting mechanism, and bringing the joint lock mechanism of the robot arm into a secured state upon carrying out the impedance control on the body unit shifting mechanism.

10. A robot control method for controlling an operation of a robot comprising: a base unit; a body unit; a body unit shifting mechanism that connects the base unit to the body unit so as to relatively shift the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the joint of the robot arm so as to drive to pivot the plurality of links; an actuator for a waist joint, that drives the body unit through the body unit shifting mechanism so as to relatively shift relative to the base unit; and actuators for the joint lock mechanisms, that drives the joint lock mechanisms;
the method comprising: detecting an external force applied to a robot arm by an operator using an external force detection device that is disposed on the robot arm, carrying out control operations of impedance control of one of the robot arm and the body unit shifting mechanism and position control of the other one of the robot arm and the body unit shifting mechanism while successively switching between the robot arm and the body unit shifting mechanism, and bringing the joint lock mechanism of the robot arm into a secured state upon carrying out the impedance control on the body unit shifting mechanism.

11. A non-transitory computer readable medium storing thereon a robot control program for controlling an operation of a robot comprising: a base unit; a body unit; a body unit shifting mechanism that connects the base unit to the body unit so as to relatively shift the body unit relative to the base unit; a robot arm that is disposed on the body unit, and has a plurality of links and joint lock mechanisms capable of respectively mechanically securing a joint coupling the plurality of links to one another and a joint coupling one of the plurality of links and the body unit; an actuator for the robot arm, that drives the joint of the robot arm so as to drive to pivot the plurality of links; an actuator for a waist joint, that drives the body unit through the body unit shifting mechanism so as to relatively shift relative to the base unit; and
actuators for the joint lock mechanisms, that drives the joint lock mechanisms, the control program allowing a computer to function as a robot operation control unit that carries out, based upon an external force detected by an external force detection device disposed on the robot arm to detect an external force applied to the robot arm by an operator, control operations of impedance control of one of the robot arm and the body unit shifting mechanism and position control of the other one of the robot arm and the body unit shifting mechanism while successively switching between the robot arm and the body unit shifting mechanism, and brings the joint lock mechanism of the robot arm into a secured state upon carrying out the impedance control on the body unit shifting mechanism.

12. The robot according to claim 2, wherein the body unit shifting mechanism is a waist mechanism that rocks the body unit substantially forward and rearward around the waist joint relative to the base unit.

13. The robot according to claim 3, wherein the body unit shifting mechanism is a waist mechanism that rocks the body unit substantially forward and rearward around the waist joint relative to the base unit.

* * * * *